(12) United States Patent
Woo et al.

(10) Patent No.: US 7,398,171 B2
(45) Date of Patent: Jul. 8, 2008

(54) AUTOMATED QUALITY CONTROL METHOD AND SYSTEM FOR GENETIC ANALYSIS

(75) Inventors: David C. Woo, Foster City, CA (US); Yerramalli Subramaniam, Belmont, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 11/428,048

(22) Filed: Jun. 30, 2006

(65) Prior Publication Data

US 2007/0010951 A1 Jan. 11, 2007

Related U.S. Application Data

(60) Provisional application No. 60/696,127, filed on Jun. 30, 2005.

(51) Int. Cl.
*G06F 19/00* (2006.01)
*G06F 17/40* (2006.01)

(52) U.S. Cl. .......................... 702/82; 382/100; 382/128; 382/129; 382/133; 702/19; 702/20; 702/81; 702/189

(58) Field of Classification Search .................. 382/100, 382/110, 128, 129, 130, 133; 702/19, 20, 702/81, 82, 84, 189
See application file for complete search history.

(56) References Cited

U.S. PATENT DOCUMENTS

| | | | | |
|---|---|---|---|---|
| 4,125,828 A | * | 11/1978 | Resnick et al. | ............... 382/134 |
| 4,873,633 A | * | 10/1989 | Mezei et al. | ................... 356/39 |
| 5,283,018 A | * | 2/1994 | Inaba et al. | ................. 264/40.1 |
| 5,787,188 A | * | 7/1998 | Nelson et al. | ............... 382/133 |
| 6,171,793 B1 | * | 1/2001 | Phillips et al. | .................. 435/6 |
| 6,650,932 B1 | * | 11/2003 | Menzie et al. | .............. 600/513 |
| 6,694,286 B2 | * | 2/2004 | Ottosson | ...................... 702/182 |
| 7,008,789 B2 | * | 3/2006 | Gambini et al. | .......... 435/287.2 |
| 2002/0172959 A1 | * | 11/2002 | Recipon et al. | ................. 435/6 |
| 2002/0192808 A1 | * | 12/2002 | Gambini et al. | .......... 435/287.2 |
| 2003/0165916 A1 | * | 9/2003 | Sealfon et al. | ................. 435/6 |

(Continued)

FOREIGN PATENT DOCUMENTS

WO WO 96/21229 A1 * 7/1996

(Continued)

OTHER PUBLICATIONS

IBM Technical Disclosure Bulletin, "Disk File Test Equipment", Mar. 1, 1977, vol. 19, No. 10, pp. 3901-3902.*

(Continued)

*Primary Examiner*—Edward R Cosimano

(57) ABSTRACT

Aspects of the present invention describe a method and apparatus for automating quality control for gene expression data. A computer based device receives gene expression data associated with a spectral species and genetic sample in each well of a plate. Gene expression data may be received from a sequence detection instrument performing one or more gene expression related operations for each of the wells of the plate. The computer based device identifies gene expression data determined to have anomalous characteristics according to a set of one or more quality control metrics and may conditionally flag one or more wells of the plate affected by the anomalous characteristics. Filters can then be selectively applied to temporarily or permanently remove the flagged data from subsequent gene expression studies.

22 Claims, 20 Drawing Sheets

U.S. PATENT DOCUMENTS

| | | | |
|---|---|---|---|
| 2004/0003026 A1* | 1/2004 | Fukumoto | 709/201 |
| 2004/0038390 A1* | 2/2004 | Boege et al. | 435/288.7 |
| 2004/0114800 A1* | 6/2004 | Ponomarev et al. | 382/173 |
| 2004/0126782 A1* | 7/2004 | Holden et al. | 435/6 |
| 2004/0148139 A1* | 7/2004 | Nguyen et al. | 702/189 |
| 2005/0013510 A1* | 1/2005 | Leikas et al. | 382/309 |
| 2005/0240090 A1* | 10/2005 | Ruchti et al. | 600/316 |
| 2006/0204997 A1* | 9/2006 | Macioszek et al. | 435/6 |
| 2006/0235646 A1* | 10/2006 | Fathallah-Shaykh | 702/179 |
| 2006/0242522 A1* | 10/2006 | Schultz et al. | 714/736 |
| 2007/0010951 A1* | 1/2007 | Woo et al. | 702/19 |
| 2007/0011201 A1* | 1/2007 | Subramaniam et al. | 707/104.1 |

FOREIGN PATENT DOCUMENTS

| | | |
|---|---|---|
| WO | WO 01/65349 A1 | 9/2001 |
| WO | WO 02/05209 A2 | 1/2002 |
| WO | WO 03/044459 A1 * | 5/2003 |
| WO | WO 03/088090 A2 | 10/2003 |

OTHER PUBLICATIONS

Luscombe, Nicholas M et al.: "Express Yourself: A modular platform for processing and visualizing microarray data." Nucleic Acids Research, Jul. 1, 2003, vol. 31. No. 13, Jul. 1, 2003 pp. 3477-3482, XP002408731; ISSN: 1362-4962—relevant passages include the whole document.

Palsson B, et al. "Using Quality Measures to Facilitate Allele Calling In High-Throughput Genotyping." Genome Research. Oct. 1999, [Online] vol. 9, No. 10 Oct. 1999, pp. 1002-1012, XP002408730 ISSN: 1088-9051 Retrieved from the Internet URL:http://www.genome.org/cgl/reprint/9/10/1002 (retrieved on Nov. 23, 2006) p. 1002-p. 1003.

* cited by examiner

FIG. 3B

Analysis Settings for Plate 96well10672105

Plate | Detector

Flag Condition and Omit Settings:

| Flag Condition and Omit Plates When... | Flag Condition | Condition | Flag ... | Omit |
|---|---|---|---|---|
| Fluorescence is off-scale (FOS) | ▽ | | | ☐ |
| A well has missing data (HMD) | ▽ | | | ☐ |
| Laser power is low during the run (LPL) | ▽ | > | 2000 | ☐ |
| Large mean squared error is (LME) | ▽ | > | 60 | ☐ |
| Percentage of plate wells not amplified (NAP) | ▽ | | | ☐ |
| A well is empty (EW) | ▽ | > | 0.6 | ☐ |
| Bad passive reference signal (BPR) | ▽ | < | 5 | ☐ |
| A well is not amplified (NAW) | ▽ | > | 1 | ☐ |
| A well has a noise spike (HNS) | ▽ | > | 4 | ☐ |
| A well has high relative noise (HRN) | | | | |

☐ Save Settings As My Default      Restore Factory Settings

OK      Cancel      Apply

FIG. 3C

AUTOMATED QUALITY CONTROL METHOD AND SYSTEM FOR GENETIC ANALYSIS

CROSS-REFERENCE TO RELATED APPLICATIONS

This application is related to and has an effective filing date of now expired Provisional Application No. 60/696,127, filed Jun. 30, 2005 assigned to the assignee of the present invention entitled, "Flagging and Filtering of Gene Expression and Genotyping" by Yerramalli Subramaniam, Madhu Augustine, David Woo and Jacob Burghardt, which is incorporated herein by reference.

INTRODUCTION

Conventional gene expression results produced using real-time polymerase chain reaction (RT-PCR) generally requires extensive review by scientists before use in studies. During the review, scientists engage in the tedious and laborious process of eliminating poor data points, experimental failure and other items that may contribute to unreliable results from the RT-PCR data. This process of quality-control or QC is an important aspect of the experiment as it eliminates non-usable data points and improves the reliability of the overall experiment or associated study.

Unfortunately, larger experiments and sample sizes are rapidly making it cost prohibitive to perform meaningful QC manually. Increased well count of sample plates from 96-well plates to 384-well plates have increased the sheer volume of data collected by a factor of 4. The volume of information can no longer be feasibly reviewed manually in a reasonable time or for acceptable costs. Future systems will undoubtedly result in even higher well-density on the plates and increased QC issues surrounding data collection.

Uniformity in implementing QC is also problematic for large amounts of gene expression data. In these large experiments, QC responsibilities may be divided and performed by a team of individuals rather than a single scientist. Each person on the team may evaluate the gene expression data and reach different conclusions. In some cases, one scientist may discard certain data gathered as inaccurate while another scientist may use slightly different criteria and keep the results. In high volume throughput systems, this eventually may lead to either losing important data or conversely introducing other errors in the data collected.

Accordingly, it is desirable to improve the quality control for data derived from various types of experiments and used in gene expression and other types of analysis.

BRIEF DESCRIPTION OF THE DRAWINGS

The skilled artisan will understand that the drawings, described below, are for illustration purposes only. The drawings are not intended to limit the scope of the present teachings in any way.

FIG. 3B depicts a graphical user interface (GUI) for controlling the quality control (QC) metrics and the resulting flagging and filtering operations they perform according to various implementations of the present invention;

FIG. 3C depicts a graphical user interface (GUI) to view flag and filtering as performed in accordance with various implementations of the present invention;

SUMMARY

Aspects of the present invention describe a method and apparatus for automating quality control (QC) for gene expression data. Typically, a computer-based device receives gene expression data associated with at least one spectral species and genetic sample in each well of a plate. Gene expression data may be received from a sequence detection instrument performing one or more gene expression related operations on each of the wells of the plate. The computer-based device identifies gene expression data determined to have anomalous characteristics according to a set of one or more QC metrics. The results from these tests are used to conditionally flag wells of the plate affected by the anomalous characteristics according to various selected QC metrics. Filters can then be selectively applied to temporarily or permanently exclude the flagged data from subsequent gene expression studies.

Other aspects of the present invention describe a method of interfacing with a system used to perform quality control on gene expression data. The interface may be displayed on a graphical user interface (GUI) running on a computer or computer-like device and receive control commands through a keyboard, mouse and other like devices. The interface used by the system graphically depicts a plate having one or more wells and their contents with a matrix of elements addressable along at least two-dimensions. Each of the one or more elements in the matrix is distinguishable based upon the passing and or failing of one or more QC metrics for gene expression data.

A combination of colors and shapes can be used to flag some elements in the matrix as passing or failing certain QC metrics. For example, a first geometric shape can be used to mark an element in the matrix when the well has passed all quality control metrics and a second geometric shape when the well has not passed all the quality control metrics specified for the well. The interface also allows a user to control filtering of values associated with the distinguished one or more elements in the matrix. Filtering may be applied selectively in response to the one or more quality control metrics and to improve analysis of the gene expression data.

These and other features of the present teachings are set forth herein.

DESCRIPTION

Figure 1:
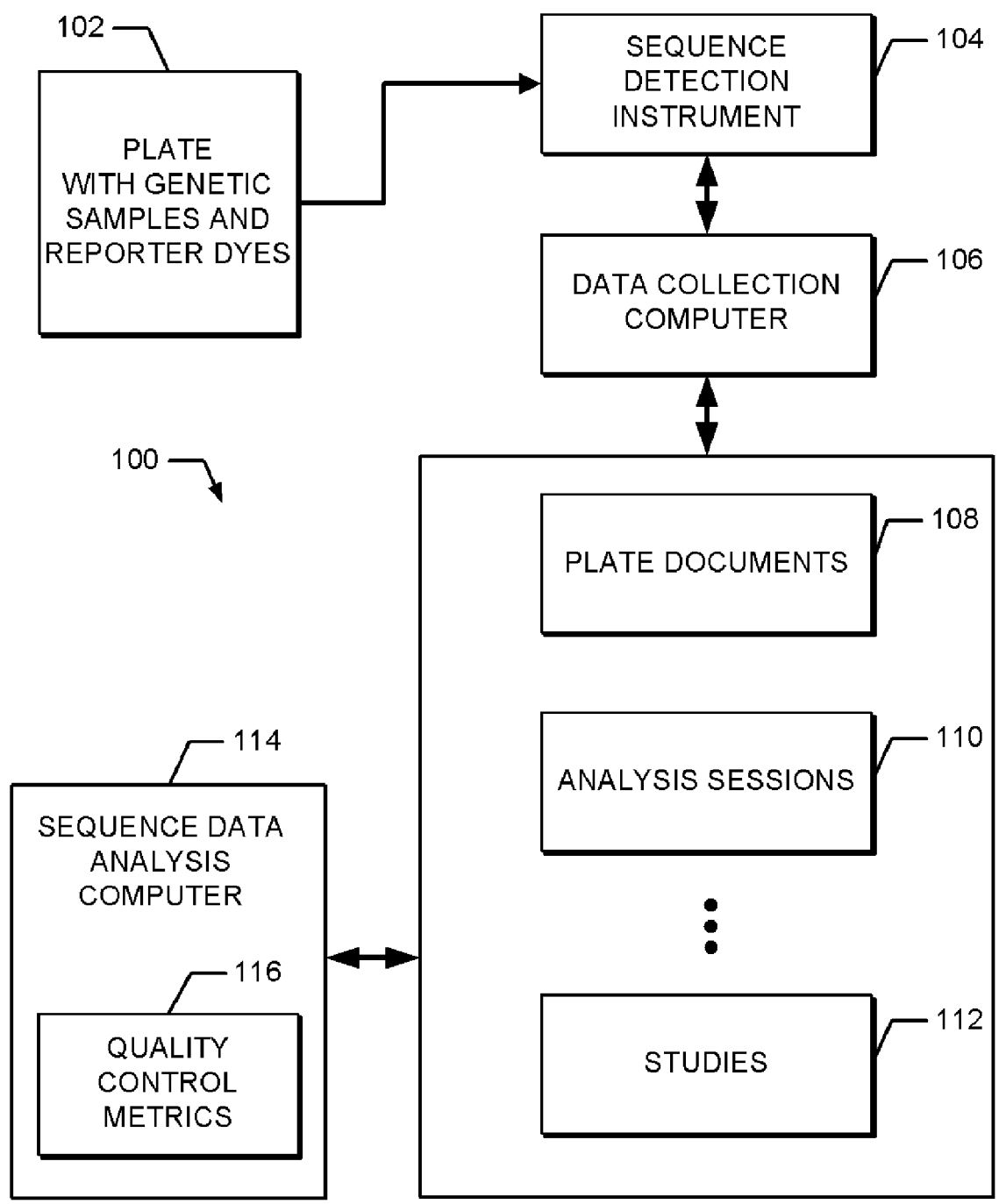
FIG. 1 is a schematic illustrating a system for spectral detection and analysis in accordance with various implementations of the present invention.

FIG. 1 is a schematic illustrating a system for spectral detection and analysis in accordance with some implementations of the present invention. System 100 includes a plate 102 with genetic samples, a sequence detection instrument 104, a data collection computer 106, plate documents 108, analysis session 110, a studies 112 containing analytical results from many plates and a sequence data analysis computer 114. To improve the quality of information being processed, sequence data analysis computer 114 further utilizes one or more quality control (QC) metrics 116 to flag and filter gene expression data taken both from the plate documents 108 and the studies 112 repositories.

Sequence detection instrument 104 includes a spectral detector capable of distinguishing certain spectral species emitted from the fluorescence of reporter dyes interacting with the genetic material in wells on plate 102. The spectra is typically monitored in real-time as a thermal cycler in the sequence detection instrument 104 performs PCR on the genetic material. For example, PCR operations may cause the sample or target genetic material to replicate and hybridize with increasing amounts of a SYBR green dye detectable in the wells of plate 102. After several thermal cycles, the concentration of the target increases along with a detectable rapid increase of fluorescence from the SYBR green dye or other reaction substrate. A cycle threshold or Ct measurement is then identified when the measure of fluorescent intensity increases linearly on a logarithmic scale compared with the increasing cycle number. Subsequent analysis of Ct values among various reactions may be used to identify a concentration of the target genetic material.

Data collection computer 106 gathers raw data provided by sequence detection instrument 104 and stores in plate documents 108 as required by a particular study or experiment being performed. The raw data is labeled, organized and stored by data collection computer 106 in one of several different storage areas or files for subsequent processing. For example, the example in FIG. 1 depicts data collection computer 106 as capable of storing the raw data in as plate documents 108 or studies 112. In some cases, data collection computer 106 may also perform certain calibration operations or other types of basic data analysis with the results to be stored in analysis sessions 110.

Resulting data stored in plate documents 108, studies 112 and analysis sessions 110 are then made available to sequence data analysis computer 114. Operations in sequence data analysis computer 114 not only may perform further computational analysis but also perform and produce quality control or QC metrics 116 on the stored data in order to improve overall results. In particular, aspects of the present invention provide QC metrics 116 to help ensure the data used in the gene expression analysis has not been tainted by unforeseen events or equipment malfunctions. For example, some events affecting the gene expression analysis may include the physical failure of one or more wells in plate 102, mismatched components in system 100, improper calibration or setup and many other causes.

In operation, system 100 uses QC metrics 116 to flag anomalous data gathered from plate 102 and then selectively filter or eliminate the data. A user can setup various filtering conditions based upon the results from QC metrics 116 and readily automate the QC process. In some cases, the filtering conditions can be triggered based on the detectable presence of a certain condition while in other cases QC metrics 116 may continuously monitor other data and only filter certain data that meets or exceeds certain filtering threshold requirements. For example, a set of wells in plate 102 may be detected and flagged by QC metrics 116 as meeting nominal QC characteristics yet insufficient for filtering or elimination. It is contemplated that use of QC metrics 116 to flag and filter improves the quality of the data analysis and may increase the throughput of analysis through automation. This is particularly important as well-densities of plates holding samples increase and sensors become more sensitive to smaller variations in signal.

Figure 2:
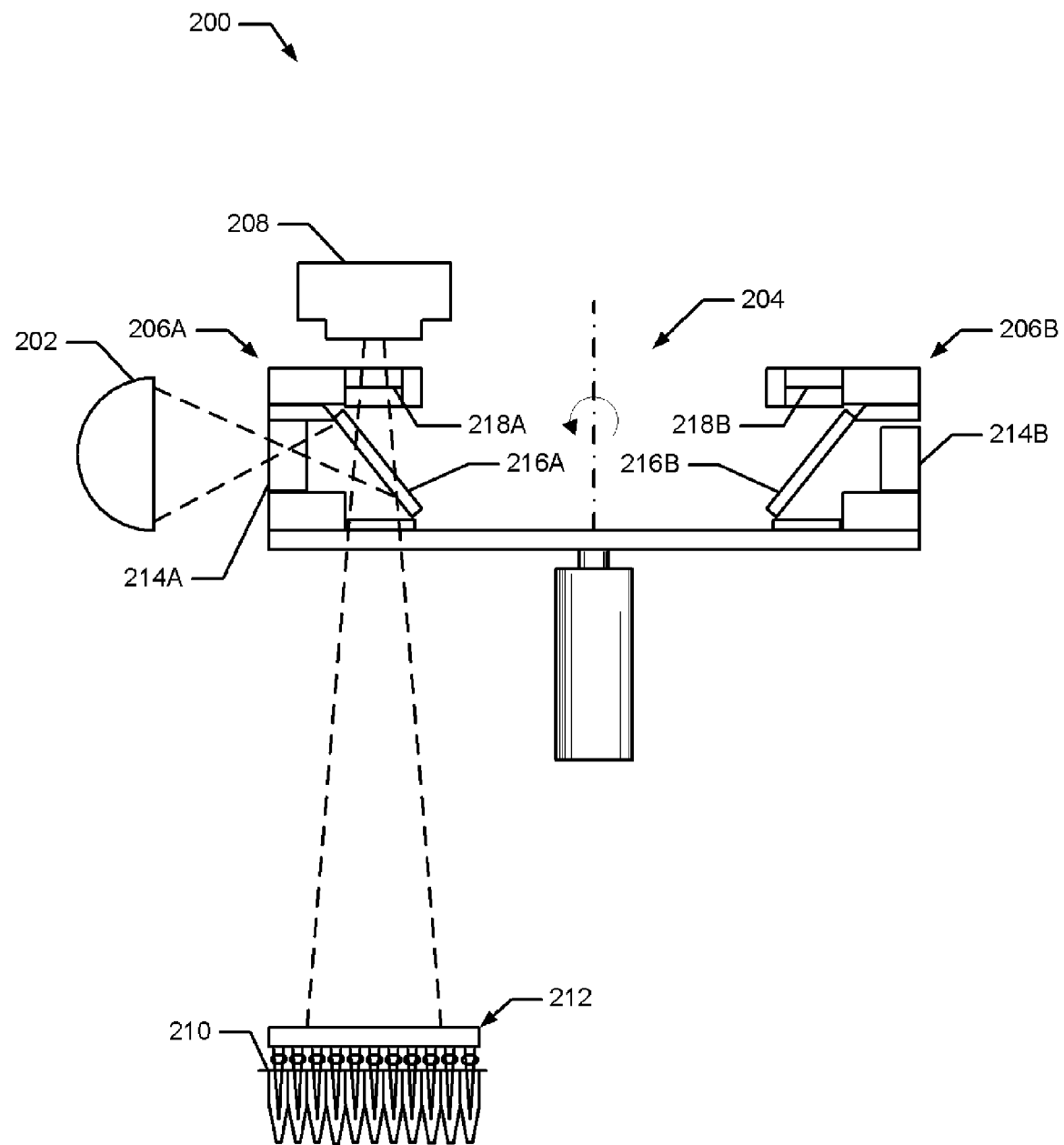
FIG. 2 is a schematic illustration of a system used for fluorescent signal detection in accordance with various implementations of the present invention.

FIG. 2 is a schematic illustration of a system 200 used for fluorescent signal detection in accordance with implementations of the present invention. This illustration depicts certain features typically associated with the Applied Biosystems 7500 Real-Time PCR System. However, various aspects of the invention can be used in conjunction with the Applied Biosystems 7900HT Fast Real-Time PCR System model as well as almost any other device involved with gathering and/or analyzing spectra from a sample.

Accordingly, detection system 200 illustrates some of the components making up the spectral detector and optics in sequence detection instrument 104 previously described in FIG. 1. Detection system 200 can be used with real-time PCR (RT-PCR) processing in conjunction with aspects of the present invention. As illustrated, detection system 200 includes a light source 202, a filter turret 204 with first filter cube 206A and second filter cube 206B, a detector 208, a microwell fray 210 and well optics 212. The first filter cube 206A can include an excitation filter 214A, a beam splitter 216A and an emission filter 218A corresponding to one spectral species selected from a set of spectrally distinguishable species to be detected. The second filter cube 206B can include an excitation filter 214B, a beam splitter 216B and an emission filter 218B corresponding to another spectral species selected from the set of spectrally distinguishable species to be detected.

Light source 202 can be a laser device, Halogen Lamp, arc lamp, Organic LED, an LED lamp or other type of excitation source capable of emitting a spectra that interacts with spectral species to be detected by system 200. In this illustrated example, light source 202 emits a broad spectrum of light filtered by either excitation filter 214A or excitation filter 214B that passes through beam splitter 216A or beam splitter 216B and onto microwell tray 210 containing one or more spectral species. Further information on light sources and overall optical systems can be found in U.S. Pat. No. 7,008,789 entitled "Instrument for Monitoring Polymerase Chain Reaction of DNA", by Gambini et al. and U.S. patent application Ser. No. 10/440,719 and Publication No. 2004/0038390 entitled "Optical Instrument Including Excitation Source" by Boege et al. and assigned to the assignee of the present case.

Light emitted from light source 202 can be filtered through excitation filter 214A, excitation filter 214B or other filters that correspond closely to the one or more spectral species. These spectrally distinguishable species may include one or more of FAM, SYBR Green, VIC, JOE, TAMRA, NED, CY-3, Texas Red, CY-5, Hex, ROX (passive reference) or any other fluorochromes that respond by emitting a detectable signal. In response to light source 202, the target spectral species and selected excitation filter, beamsplitter and emission filter combination provide the largest signal response while other spectral species with less signal in the bandpass region of the filters contribute less signal response. Multicomponent analysis is typically used to determine the concentration of the individual species according to their respective contribution to the emitted spectra.

Referring to FIG. 2, microwell tray 210 generally contains the genetic target sample with one or more reporter dyes corresponding to the assay used in conjunction with an experiment. Microwell tray 210 can include a single well or any number of wells however typical sets include 96-wells, 384-wells and other well configurations. Of course, experiments may be designed to use many other plate configurations having different multiples of wells other than 96. The sample and particular combination of dyes used in the selected assay may be sealed in microwell tray 210 using heat and an adhesive film to ensure they do not evaporate or become contaminated.

Detector 208 receives the signal emitted from spectral species in microwell tray 210 in response to light passing through the aforementioned filters. Detector 208 can be any device capable of detecting fluorescent light emitted from multiple spectrally distinguishable species in the sample. For example, detector 208 can be selected from a set including a charge coupled device (CCD), a charge induction device (CID), a set of photomultiplier tubes (PMT), photodiodes and a CMOS device. Information gathered by detector 208 can be processed in real-time in accordance with implementations of the present invention and through subsequent post-processing operations for performing calibration and QC metrics in accordance with various aspects of the present invention.

High throughput systems can use additional quality control processing to flag and/or potentially eliminate anomalous data results. QC metrics designed in accordance with aspects of the present invention further analyze patterns and conditions in the data to facilitate this process. As will be described in further detail later herein, the type of experiment and the assay used in the gene expression or genotyping operation may influence the selection of QC metrics and the flagging and filtering of data. To increase the usability of these QC metrics, templates can be established for the automatic flagging and filtering of different datasets depending on the type of experiment and the lab protocol established for the experiment. Each template can specify a predetermined combination of QC metrics for a study. Instead of specifying individual QC metrics, the study can specify a template of predetermined QC metrics. This can reduce human error and increase uniformity in the data analysis portion of the study.

Figure 3A:
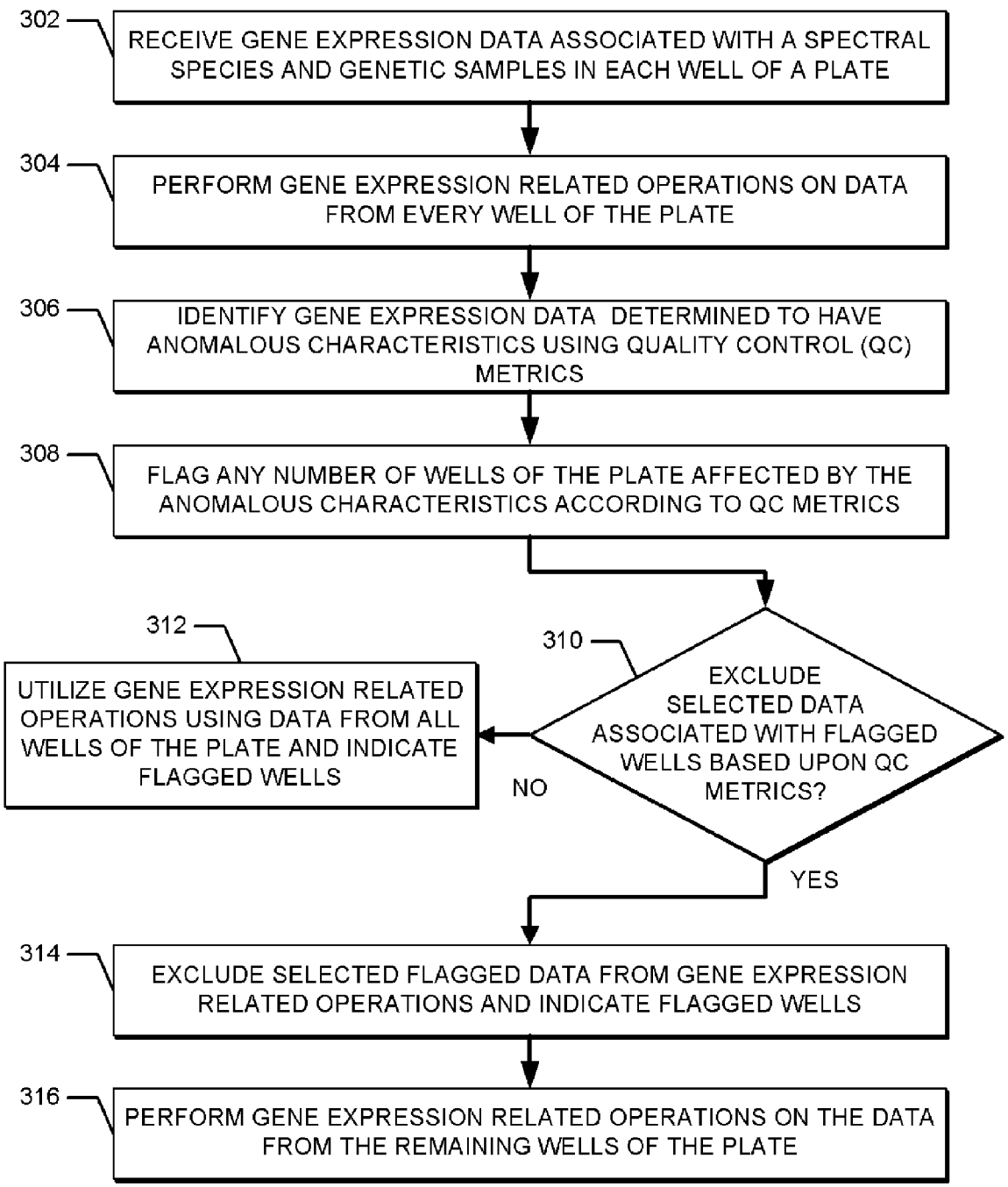
FIG. 3A is a flowchart diagram of operations to flag and filter gene expression data as part of quality control (QC) in accordance with various implementations of the present invention.

FIG. 3A is a flowchart diagram of operations to flag and filter gene expression data as part of a quality control in accordance with various implementations of the present invention. It is understood that a single pass of the flowchart diagram steps is provided even though one or more of the steps may be performed in a different order, repeatedly or at least until the QC metrics have filtered the anomalous data set values. Initially, the QC metrics receive gene expression data associated with a spectral species and genetic samples in each well of a plate (302). As previously described, the gene expression data is typically the raw data collected by the sequence detection system and data collection computer during RT-PCR. In some cases, one or more calibration operations may be performed on the gene expression data to compensate for systematic error or other detectable peculiarities of the system.

Next, implementations of the present invention perform one or more gene expression related operations on data from every well of the plate (304). It is contemplated that the one or more gene expression related operations may encompass a wide-range of possibilities. In some cases, the type of operations may depend on the type of experiment being performed and the type of assay used to measure the resulting genetic quality. For example, one set of assays may be used for allelic discrimination experiments while absolute quantification experiments may use another. QC metrics may capture the results from a Ct determination for further consideration before the Ct value for a given reaction is actually generated.

QC metrics designed in accordance with aspects of the present invention then identify gene expression data determined to have anomalous characteristics (306). Some of the tests performed by the QC metrics include: sensor saturation analysis, bad passive reference analysis, missing data analysis, empty well analysis, large composite signal error analysis, low-laser power analysis, non-amplified well analysis, non-amplified plate analysis, a noise spike analysis, a high-relative noise analysis, a distance between clusters analysis, Ct failure analysis, a number of clusters analysis, exponential region failure analysis, a Hardy-Weinberg analysis, a proportion of outliers analysis, a small sample number in cluster, baselining failure analysis, and thresholding analysis.

Each of these different tests provides an indicator as to the quality of the data collected from a well in plate or several plates in a study. QC metrics generally flags one or more wells of the plate affected by the anomalous characteristics (308). If the data in a well meets several tests from the QC metrics then several flags are associated with the well for each of the tests.

It is also possible that the wells and plates are part of different studies and therefore the plates and studies may also be flagged with these tests results as well. In other words, a complete study may be flagged with multiple flags rather than a single flag. This allows quality control data results to be considered for each well in a plate, each plate in a study or to compare one study with another. In addition to these groupings, it is contemplated that the flags can be used in data-mining and exploring other possible trends and systematic errors spanning a variety of different wells, plates and studies potentially spanning across different datasets and experiments.

Next, the QC metrics determine if it is appropriate to exclude selected data associated with flagged wells (310). The QC metrics can be programmed with default configuration settings to perform certain tests and then simply filter or exclude the flagged results. In some cases, a nominal result from the QC metrics indicates that the data gathered is not reliable and should be both flagged and filtered from further gene expression operations (314). In these situations, the QC metrics are simply looking for the presence of a certain qualitative condition in the data to flag the well and then filter the results. For example, if the QC metrics determines that a well is empty then it would make sense to omit the results from the well as they would skew the gene expression calculations being performed on the other wells containing actual genetic material and/or reporter dyes.

Once the flagged data in the well is excluded, the gene expression related operations are performed again on the data from the remaining wells of the plate (316). By excluding the data deemed unreliable, it is contemplated that the gene expression related operations will improve and have more accurate results. For example, excluding a well in a plate as lacking specified genetic material or being empty may result in a more accurate identification of a Ct or other important gene expression values.

Other cases using the QC metrics may flag certain wells or studies from a test yet not filter the data, as the test results are considered quantitatively insufficient for filtering (312). The configuration of the QC metrics in this latter case may be set up to operate using a continuous measure of results and threshold values to indicate when to flag a results and when to both flag and filter a result from the data. It is also possible that the QC metrics is unable to identify even a nominal result from the test and therefore may neither flag nor filter the resulting well, plate and/or study. In either case, the QC metrics will generally indicate the wells that have been flagged but may only exclude certain data depending on the criteria for filtering or excluding the data collected from the wells (312).

Referring to FIG. 3B, a graphical user interface (GUI) provides a method of controlling the QC metrics and the resulting flagging and filtering operations they perform in accordance with various implementations of the present invention. In this example implementation, a QC control panel 318 includes a list of QC metrics 320, QC flag-filter conditions 322 and panel operators 324.

Each QC metric performed in this example is listed under QC metrics 320. However, it is contemplated that aspects of the present invention may also include greater or fewer QC metrics other than the ones specifically listed as long as the analytic bears some relationship to identification and removal of anomalous data from gene expression operations. In this example, there are ten (10) different QC metrics that may be performed if it is deemed appropriate for the experiment and assay. While it is not indicated specifically, the QC metrics may be performed in the order they are listed or may be reordered in the event the analysis results depends on the order or has other order-dependent characteristics or results.

QC flag-filter conditions initially may have default factory settings to give some basis for performing the flagging and filtering operations. Later, these QC flag-filter conditions 322 can be set individually and customized to the particular experiment, assay and quality control goals. Checking the "Flag Condition" box identifies the tests that the QC metrics will perform using the specified condition. For example, "Large Mean Square" (LME) has the "Flag Condition" checked and a ">" (greater than) condition with a value of 2000. Accordingly, this would mean that finding a LME value for a particular well greater than 2000 should result in filtering or excluding the data value from subsequent genetic expression operations and calculations. This helps reduce further inaccuracies into the various gene expression operations and calculations. In contrast, specifying no conditions requires only a nominal value for the QC metric to be met and a flag to be set. For example, the QC metric labeled "A well has missing data (HMD)" requires only a nominal value for the QC metric to be met and therefore the flag for a well is set as soon as the empty well condition is detected.

Unchecking the "Flag condition" box for a particular QC metric omits the test from being performed on the data. This may not only reduce processing time but also ensures that data from certain wells in a plate are not inadvertently filtered or omitted if they are found to meet the minimum conditions specified. In some alternate implementations, the QC metric is still performed even when the flag condition is unchecked but no filtering of data is performed. Instead, it is up to the operator of the detection system to manually remove the flagged data or ignore the flag and continue with the various gene expression operations in the experiment.

Figure 3C:
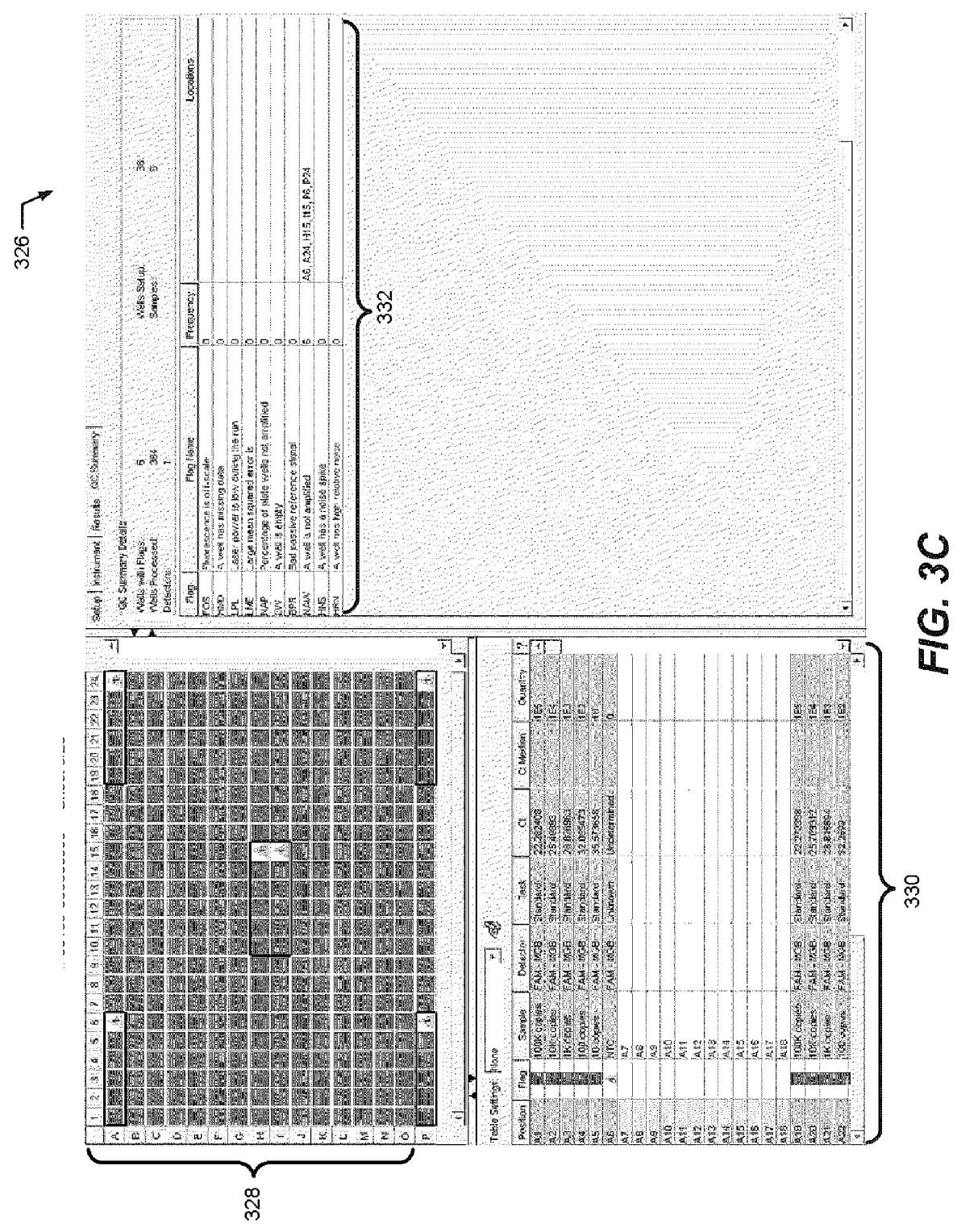

FIG. 3C depicts a graphical user interface (GUI) to view flag and filtering as performed in accordance with various implementations of the present invention. In this example, a flag and filter GUI 326 illustrates a matrix 328 representing a plate, table settings 330 with characteristics for each well and a QC summary 332 providing an overview of the quality control results. Matrix 328 contains one element for each well in a plate addressable along two-dimensions—an x and y coordinate—and one or more flags set for the particular well.

Each QC metric is capable of independently flagging a well and therefore it is possible that a single well may contain multiple or many different flags. As illustrated, matrix 328 indicates that wells A6, A24, H15, I15, P6 and P24 have all failed one ("1") QC metric test. It is contemplated that multiple numeric values could be displayed for each element and well in the plate. For example, selecting or rolling over each element in matrix 328 with a mouse or other pointer device produces a display in a tooltip or other graphical representation of the multiple QC metric values that the sample held in the corresponding well had failed.

It is also possible that matrix 328 represents an overall study and each element represents an aggregate of QC results for a complete plate. Numbers indicated on each element of matrix 328 may be used to provide an aggregate of the flags identified for all the wells in the selected plate in the study. Once again, by selecting an element in matrix 328 a tool-tip or other interface device may indicate the list of flags corresponding to the QC metrics associated with the plate in question. The operator of the computer analyzing the detection system results can consider the QC metric values being displayed in subsequent portions of the analysis in the study.

If more detailed information is desired, the operator selects an element in matrix 328 causing another matrix appear that represents one plate in the study. This additional matrix then details each plate with wells and corresponding flags as previously described. For example, an operator of the computer can single click a mouse-device over an element in a matrix representation of a study to get a visual summary of the flags set and then double-click the specific element to see an additional matrix with a detailed visual representation of the plate and corresponding wells with flags.

Certain visual effects can also be used in conjunction with matrix 328 to improve the identification and analysis of data. In large complex experiments, it is important to present information in a consistent and recognizable manner to decrease possible misreading of data and introduction of possible operational errors. This is especially true in laboratories with different people running experiments over many days, months and potentially years. Accordingly, a color system may be implemented to identify an outcome of each QC metric and the corresponding element of matrix 328. For example, a well passing all QC metrics can be labeled with a "green" color while a "red" color indicates that not only did the well not pass one or more QC metrics but that the associated data was omitted or excluded. Further, a "yellow" color can be used to identify a well that has been flagged yet the data has not been excluded. This may occur if the particular QC metric was to be omitted from the testing or not associated with the given assay or experiment at hand.

Shapes can also be used in conjunction with colors to ensure that information is conveyed accurately and quickly. A rectangular shape can be used to indicate that a well has not been excluded while a triangular shape in the element on matrix 328 can indicate that the underlying data has been excluded. This may be important if images of the matrix 328 are printed on non-color printers or the person has difficulty distinguishing from one color or the other.

These color, shape and numeric details added to matrix 328 make the GUI easier to use and reduces potential errors. For example, marking an element in the matrix with a first geometric shape and a first color can be used to indicate that the well has passed both specified and unspecified QC metrics. Meanwhile, marking an element in the matrix with a first geometric shape and a second color can be used to indicate that the well has passed the specified QC metrics but failed the unspecified QC metrics. Finally, marking an element in the matrix with a second geometric shape and a second color can be used to indicate that the well has failed to pass both specified and unspecified QC metrics. In general, it should be appreciated that associating QC metric results with various combinations of particular shapes, colors and numeric values may reduce or eliminate human-error or other operational errors otherwise present and significant in large scale and high-volume experiments that need to operate with very low error rates.

Table settings 330 provide a configurable display of results in each well as represented by the elements of matrix 328. In this example, the table displays specified results for each well in a plate including: position (i.e., well position), flag (i.e., specific QC metrics detected for the well), sample name (i.e., an identifier or label that may be used to distinguish the well), detector (i.e., specific detector dyes used in well), task (i.e., a particular task being performed), Ct (i.e., cycle threshold value detected for sample in well), Ct median (i.e., a median value of Ct used in statistical calculations) and quantity (i.e., an estimated absolute copy count). It is interesting to note in this example that the well identified as "A6" is flagged as failing a QC metric and as a result the sample count is not taken. Consequently, the task and Ct value identified for well position "A6" remains undetermined.

A QC summary 332 provides a sketch of the quality control for a given plate and or study. In this example, QC summary 322 provides a "Flag" heading with an acronym for the test a "Flag Name" heading with a brief description of the test along with a "Frequency" heading that provides a frequency of occurrence for the test in the plate and/or study and a "Location" heading listing the coordinates for the entries in the plate passing the test. The operator of the detector system can use this interface portion of the GUI to quickly identified trends and potential problems as an experiment progresses. As a result of this information, the operator can decide to continue the experiment re-run certain experiments or eliminate certain plates from study and then continue performing gene expression or genotyping operations.

For example, an operator may use matrix 328 to visually see trends in the data and identify systematic errors occurring the plate. A group of entries in matrix 328 indicating empty wells may have resulted from a rupture in one or more wells or other problems in the plate. In either event implementations of the present invention can be used quickly to identify the source of these trends and either correct or re-run portions of the experiment.

Figure 4:
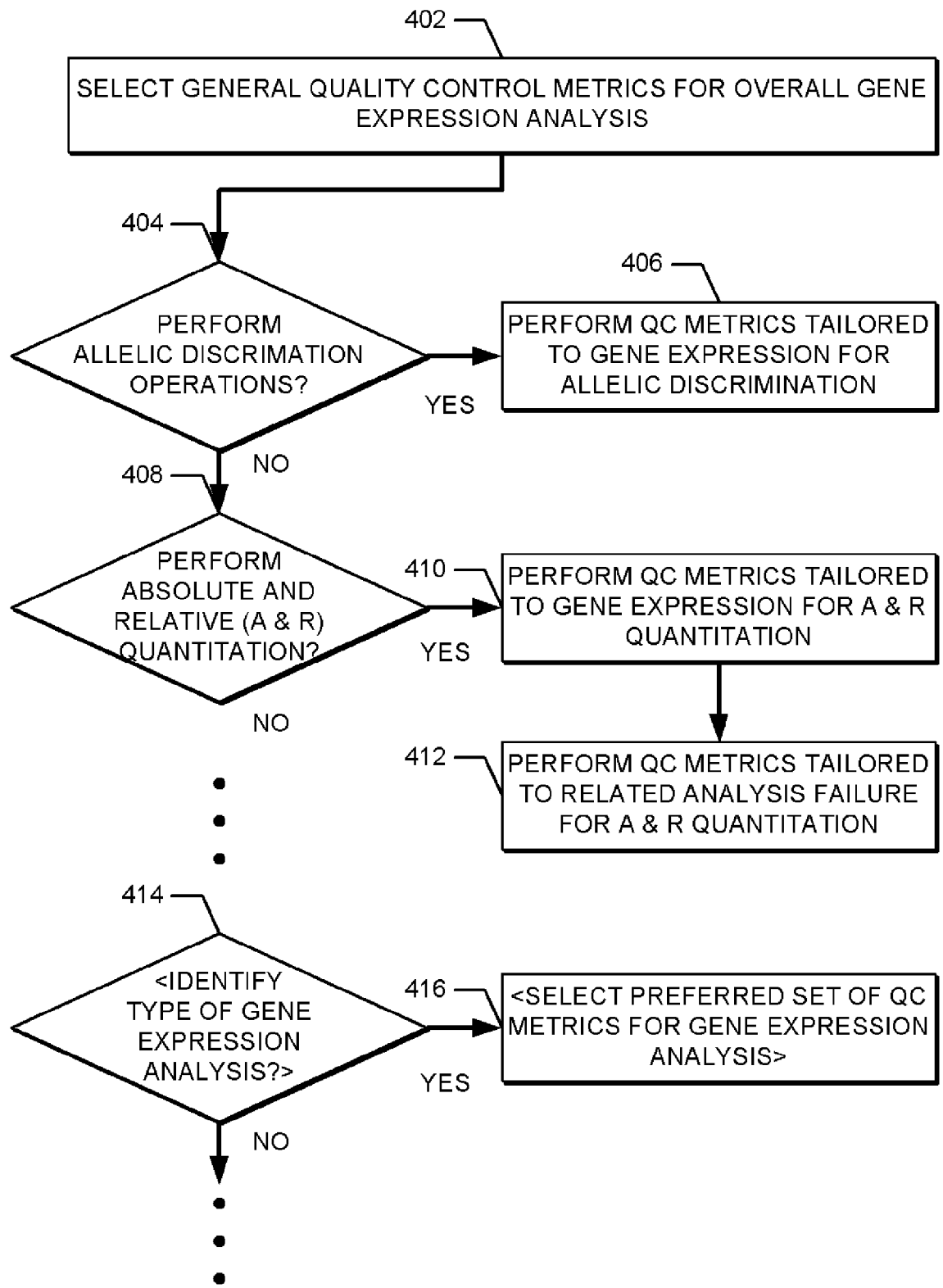
FIG. 4 provides a flowchart of the operations for selecting an appropriate set of QC metrics in accordance with various implementations of the present invention.

FIG. 4 provides a flowchart of the operations for selecting an appropriate set of QC metrics in accordance with various implementations of the present invention. In many cases, the type of QC metrics used on the results of an experiment depends on the type of experiment and the assays used to obtain the results. In this example, a detection system provides an interface for selecting general QC metrics for an overall gene expression analysis (402). General QC metrics are used for all the different experiments and assays on a given detector system and therefore are included for every QC operation. For example, one implementation may perform one or more general QC metrics that may test for fluorescence off-scale (FOS), bad passive reference (BPR), empty wells (EW), has missing data (HMD) and large mean-square error (LME). Using these QC metrics as a baseline eliminates problems that may occur in many different situations. Further details on these tests are described later herein.

Other QC metrics are selected specific to the type of experiment and assay used by the detector system. In one example implementation, performing allelic discrimination analysis (404) is associated with performing QC metrics tailored to test results of gene expression for these types of experiments. Selecting allelic discrimination analysis (404) as depicted in FIG. 4 (Yes-branch) results in performing QC metrics tailored to gene expression for allelic discrimination (406). For example, QC metrics for allelic discrimination may be selected from a set of tests including: measuring a distance between clusters (DCN) with no template control (NTC), a Hardy-Weinberg test (HW), a number of clusters (NOC) test, a percentage of outliers (POU) test and a small number of samples in cluster (SNS) test. Further details on these tests are provided later herein.

Yet another set of QC metrics are selected for testing results from both absolute and relative quantitation experiments (408). Selecting absolute and relative quantitation experiments (408) as depicted in FIG. 4 (Yes-branch) may result in performing QC metrics tailored to at least two different areas. These at least two different areas may be divided into QC metric tests for absolute and relative quantitation of gene expression (410) and QC metric tests tailored to related analysis failure for absolute and relative quantitation (412). In the former case, QC metrics for absolute and relative quantitation tailored to gene expression may include tests to identify conditions of: laser power low (LPL), non-amplified plate (NAP), non-amplified well (NAW), has noise spike (HNS) and high relative noise (HRN). In the latter case, QC metrics tailored to related analysis failure for absolute and relative quantitation (412), may test for exponential region algorithm failures (EAF), baselining algorithm failures (BAF), Ct algorithm failures (CAF) and thresholding algorithm failures (TAF).

Many other types of tests and groupings of tests are possible depending on the experiments performed and details related to the analysis of the results. Accordingly, it is contemplated that a set of QC metrics are developed in accordance with various implementations of the present invention to correspond to each different type of expression analysis. Selecting to identify a type of gene expression analysis (414) as depicted in FIG. 4 (Yes-branch) also results in selecting to perform a preferred set of QC metrics tailored to the type of gene expression analysis under consideration. In general, a set of QC metrics can be developed for any gene expression or genotyping by first identifying the type of gene expression analysis being performed (414) and then selecting a preferred set of QC metrics suited for testing the results of the gene expression analysis (416).

Specifically, a number of different QC metrics are described in further detail below. These examples illustrate the scope and variety of the various types of tests performed in one or more set of circumstances. However, it is understood that these are merely illustrative examples and aspects of the present invention should not be limited to these examples alone. Instead, it is contemplated that aspects of the present invention can use many different types of tests for QC metrics as dictated by the different gene expression experiments being performed and their results.

Figure 5:
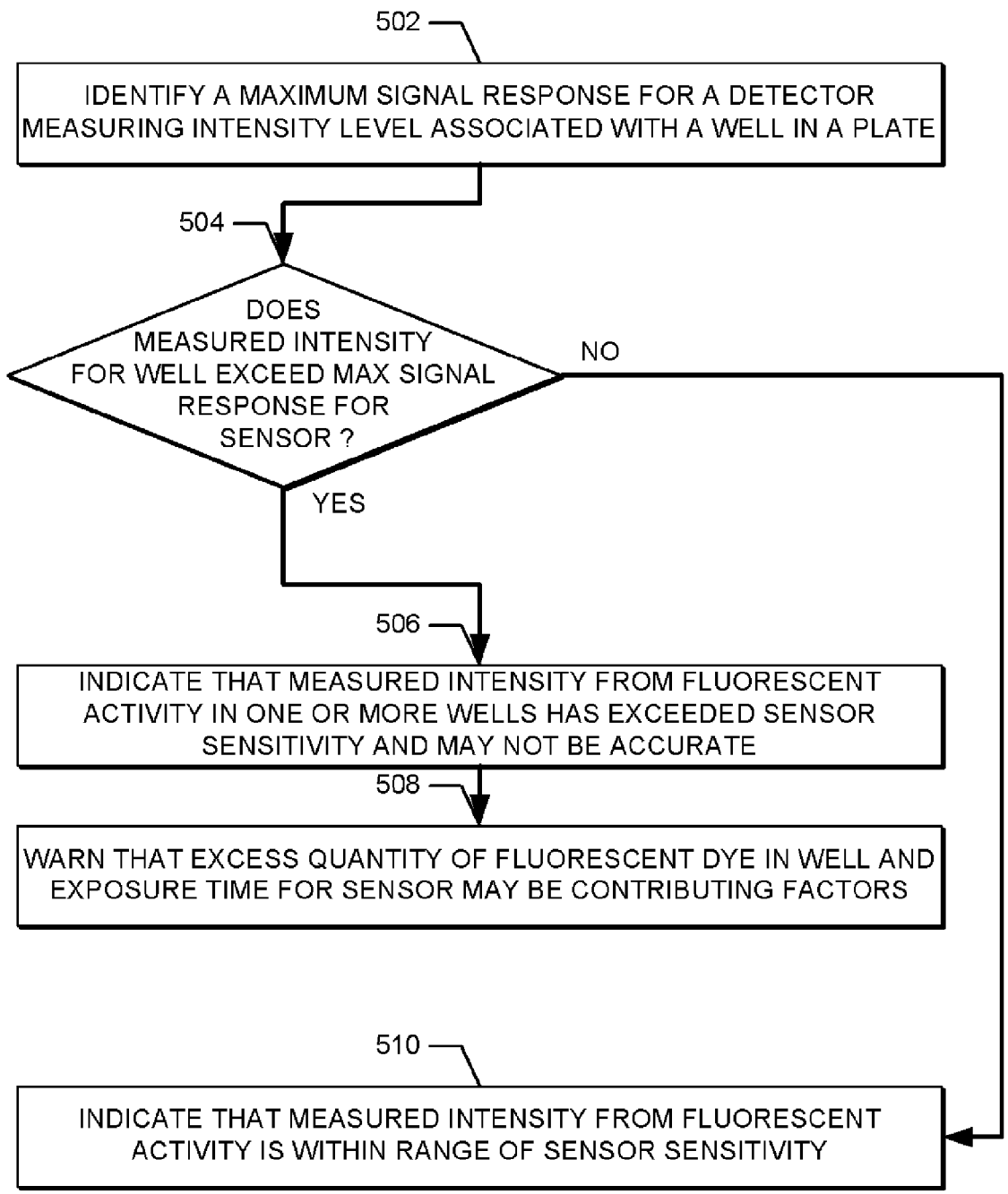
FIG. 5 depicts a flowchart diagram of the operations used to test for sensor saturation in accordance with various implementations of the present invention.

Referring to FIG. 5, a flowchart diagram depicts the operations used to test for sensor saturation in accordance with various implementations of the invention. While there may be many reasons for its occurrence, saturation generally occurs when the exposure time for a sensor is too long or when an excess amount of sample and/or dyes produce too much signal for the detector. To test for saturation, the QC metric identifies a maximum signal response for a detector when applied to a well in a plate (502). This information is generally part of the configuration information for a detector and may be stored in a memory on the detector device. Alternatively, a user may enter this information regarding sensor sensitivity when configuring the overall QC metrics for the detector.

Next, the QC metric for saturation compares each measured intensity level for each well to determine if it exceeds the maximum signal response for the sensor (504). If the intensity level does not exceed the maximum signal response rated for the sensor then the QC metric indicates that the measured intensity level from fluorescent activity is within the range of sensor sensitivity (510). Keeping the fluorescent activity within the sensors dynamic range ensures that measurement results are accurate and not beyond a level the sensor can detect.

Conversely, the QC metric may also determine that the measured intensity exceeds the maximum signal response for a sensor (504). If this occurs, the QC metric indicates that the measured signal intensity may not be accurate (506) and flags the data accordingly. Saturation is identified as intensity values that clearly exceed or come very close to a maximum sensitivity value for a sensor. For example, a signal measured as operating at the maximum signal intensity detectable by the sensor may actually be producing a greater intensity value that cannot be measured. Consequently, aspects of the present invention may flag the well and its contents as beyond the measurement capabilities of the detector. Further, aspects of the present invention, may warn the user and suggest checking for causes of the saturation including excess quantity of fluorescent dye in one or more wells and/or an overly long exposure times for the detector (508).

Figure 6:
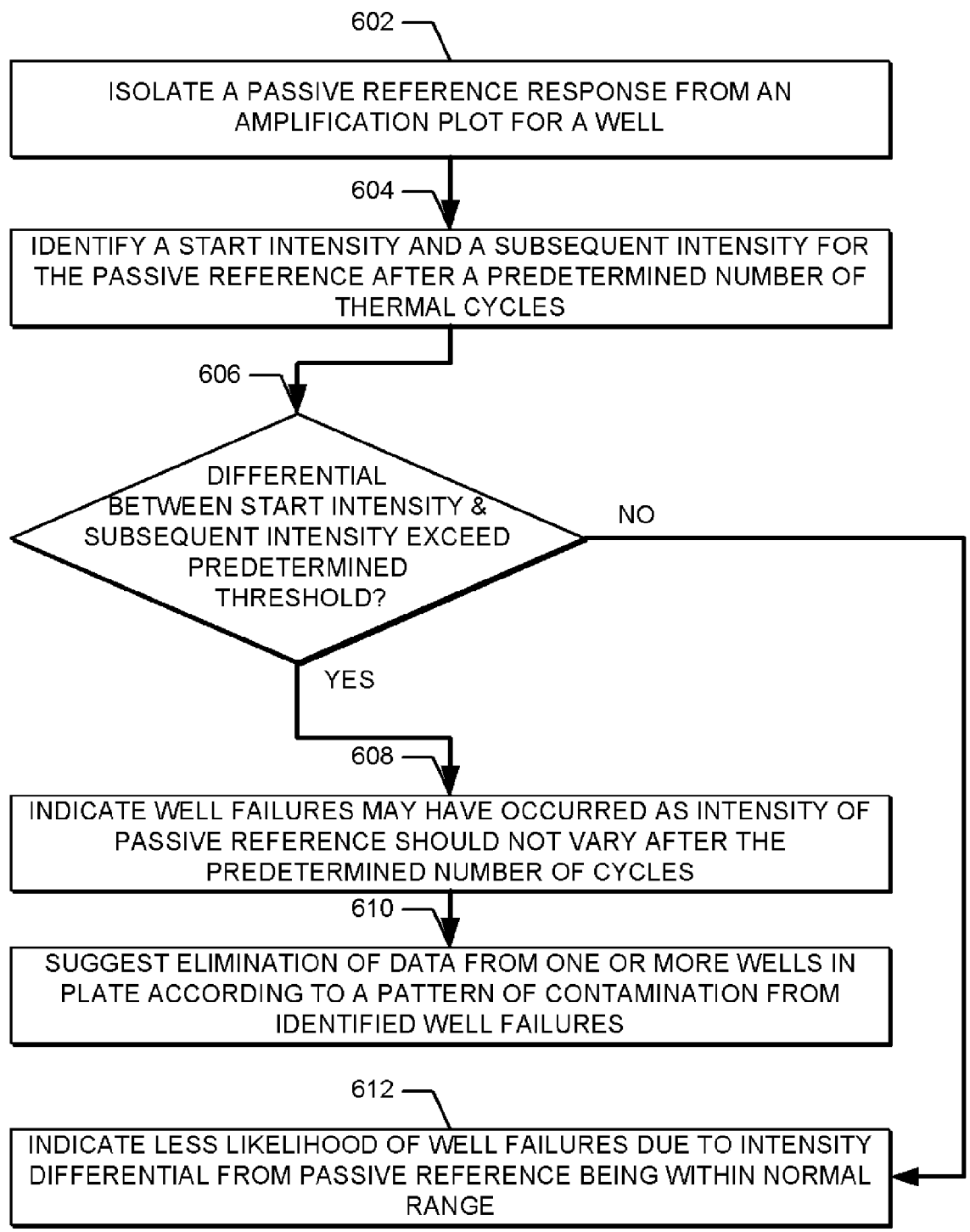
FIG. 6 depicts a flowchart for a QC metric using data measurements of a passive reference in accordance with various implementations of the present invention.

Yet another QC metric uses data measurements of a passive reference as depicted in the flowchart operations in FIG. 6. In this example, the QC metric measures intensities of the passive reference at various time intervals to identify potential well failures and other problems in a plate. Unlike the sample in a well, the passive reference during any time interval should exhibit relatively constant intensity levels during RT-PCR and other experiments. Evidence of erratic or unstable passive reference intensity can be used as a predictor that one or more wells have failed and now are either empty or partially filled.

Aspects of the present invention therefore carefully monitors the passive reference intensity changes as a thermocycler operates. The results are used to identify a failed well, a leaky well or other physical anomalies in the plate holding the samples. To identify a bad passive reference, a QC metric first isolates a passive reference response in an amplitude plot for a well (602). Typically, this involves extracting the signal waveform of the passive reference from a multicomponent plot if a passive reference, such as ROX, is mixed in the well with other dyes for normalization and other purposes.

Next, the QC metric identifies a start intensity and a subsequent intensity for the passive reference after predetermined number of thermal cycles (604). In some cases, the start intensity and subsequent intensity measurements are measured in the earlier thermal cycles while in other cases they may be measured later in the process. Taking multiple readings may be used to improve the success of this test. For example, a passive reference may not leak or collapse until multiple heat cycles of the thermal cycler have been applied.

Various implementations of the present invention compare a differential between the measured start intensity and the subsequent intensity for the passive reference with a predetermined threshold (606). For example, the predetermined threshold may be based upon selecting one or several standard deviations from a mean intensity value to derive the differential. When the differential measured is smaller or equal to the threshold there is less likelihood that the well associated with the measured data has failed or has some inherent problems (612).

Alternatively, if the differential for the passive reference intensity exceeds the predetermined threshold (606) then aspects of the present invention may flag the data associated with the particular well as having a bad passive reference and well. Well failures may be indicated when the intensity of the passive reference varies even after performance of a predetermined number of cycles (608). In addition, aspects of the present invention may also suggest elimination of data from one or more wells in the plate according to a pattern of contamination from identified well failures (610). In the case the well leaked into other wells, a single failed well may spill into other wells requiring the flagging and filtering of more than the original well identified as failing. One pattern of contamination may extend radially outward a predetermined distance from the failed well.

Figure 7:
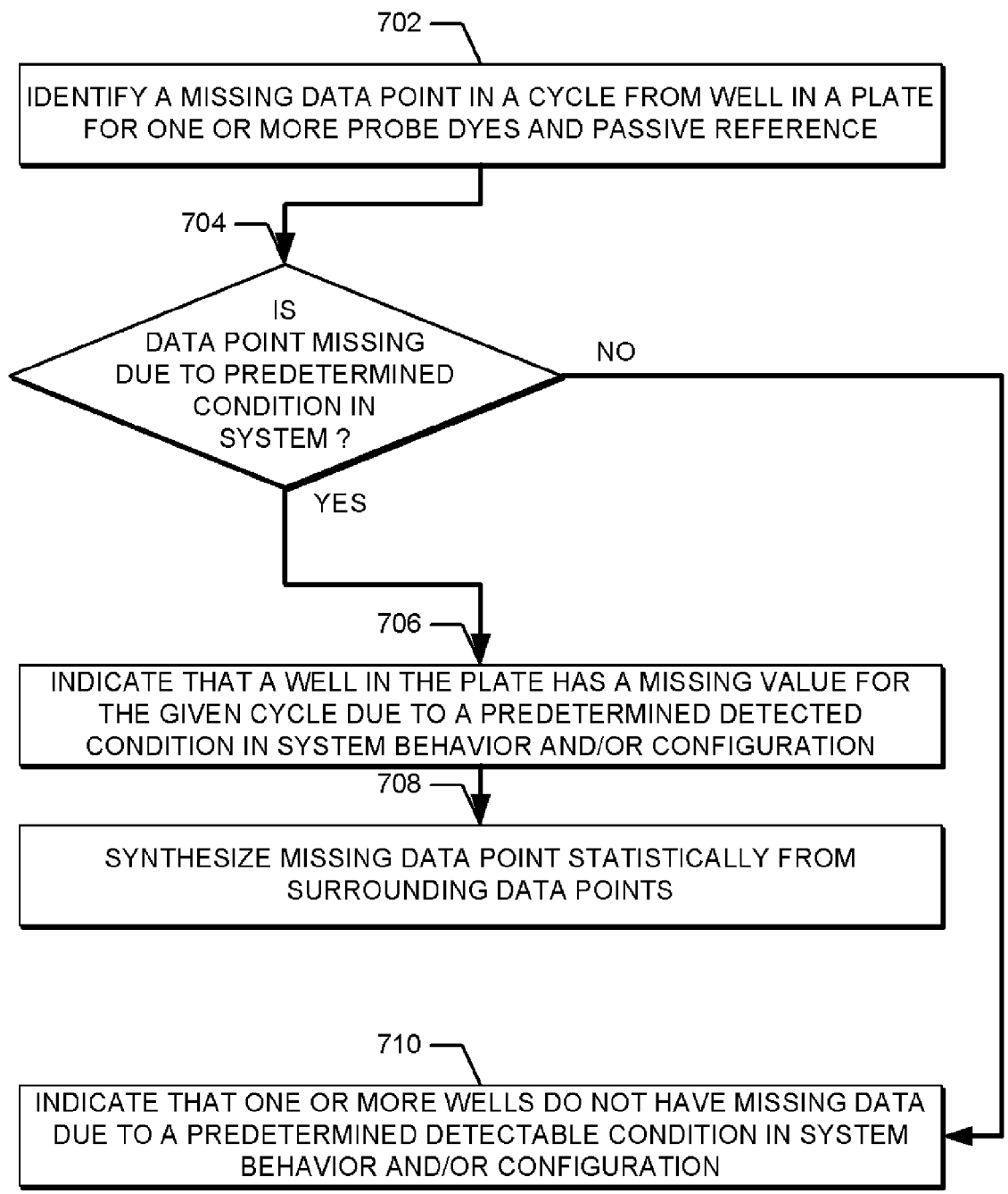
FIG. 7 is another flowchart for a QC metric that identifies one or more missing data points in a sequence of measurements taken using a detector according to various implementations of the present invention.

Another QC metric depicted in FIG. 7 identifies one or more missing data points in a sequence of measurements taken using a detector. This QC metric sequences through each data point taken for each cycle for a well in a plate and for multiple probe dyes and/or a passive reference (702). The missing data point can be identified as a sudden drop off intensities for one or several data point values followed by return of the intensity measurements.

Next, the QC metric determines if the missing data point is likely due to a timing issue in the detector and or system (704). Certain timing issues or other peculiarities may occur in the data due to mismatched firmware or software versions in the instrument, system or detector. These types of errors are generally hard to detect as they may by found surrounded by a set of otherwise acceptable data points measured by the detector. Unfortunately, a missing data point that occurs at a critical point in the amplitude curve during an experiment can skew the calculations and produce erroneous results. For example, a missing data point that occurs at or near a Ct value for an assay in RT-PCR can greatly affect the outcome of an experiment.

In this case, aspects of the present invention indicates that a well in the plate has a missing value for the given cycle due to a certain condition, system behavior, configuration or other predetermined detectable combination (706). One possible resolution is to suggest eliminating the data point from further gene expression calculations to avoid possible erroneous analysis results. Alternatively, aspects of the present invention may synthesize missing data point or points statistically from surrounding data points (708). Depending on the reliability of the synthesized data, a reliability factor can be associated with the data set associated with the well. For example, if a missing data point can be synthesized with a 90% certainty then a reliability factor of 90% may be associated with any subsequent gene expression calculations using the data. Of course, aspects of the present invention may also provide an indication that the one more wells do not have missing data due to due to anomalous system behavior and/or configuration (710).

Figure 8:
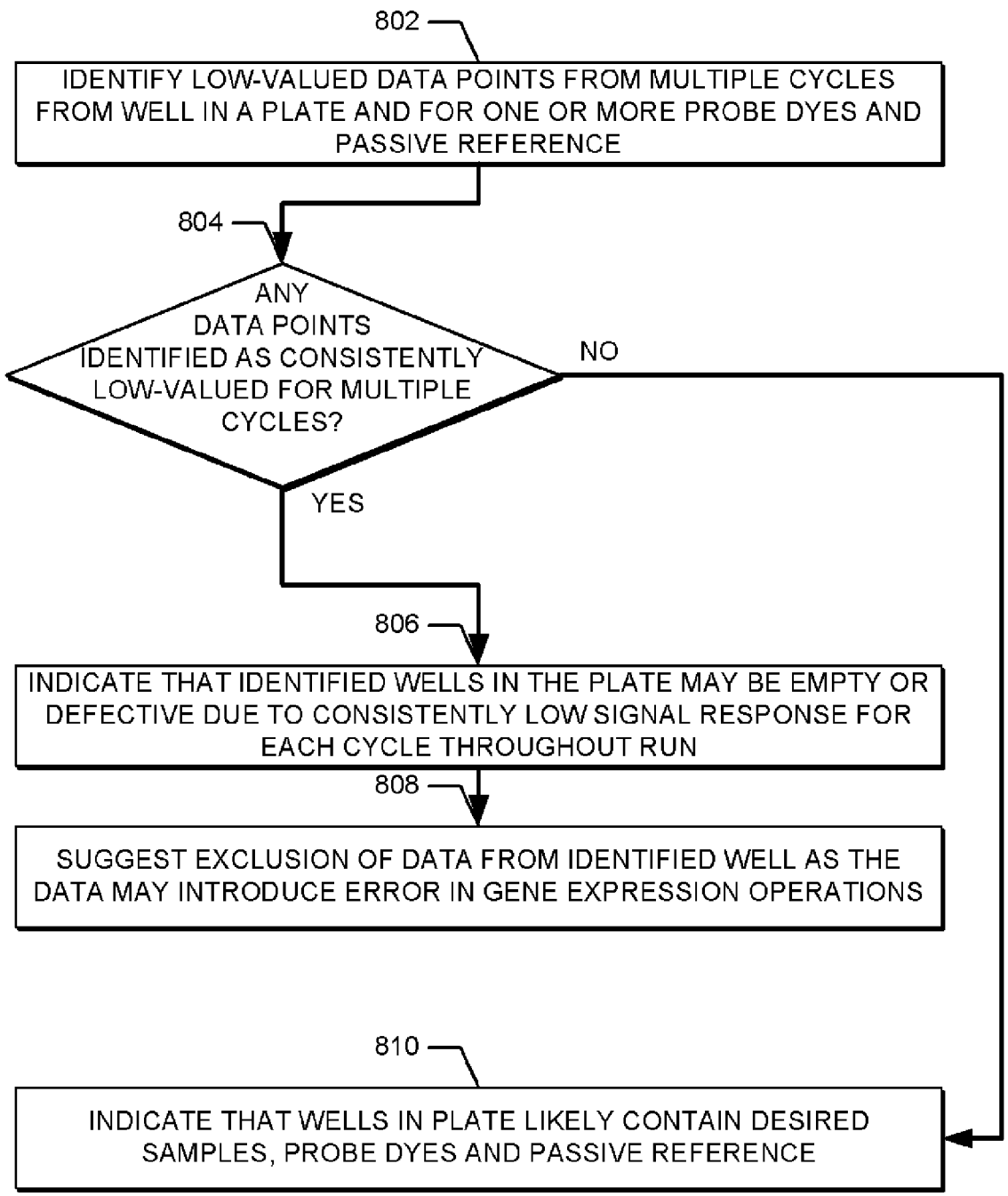
FIG. 8 depicts a flowchart of the operations for a QC metric designed to identify an empty well in a plate according to various implementations of the present invention.

FIG. 8 depicts a flowchart of the operations for a QC metric designed to identify an empty well in a plate. This test differs from the QC metric for missing data points depicted in FIG. 7 as the empty well will create data points with smaller or negligible values throughout an experiment. Plates may have empty wells when the plate is not properly prepared or when the improper type or quantity of genetic material is used. In addition, a well may also appear empty if the well in a plate leaks or otherwise becomes damaged during an experiment. Accordingly, this QC metric sequences through each data point taken during each cycle looking for multiple low-valued data points for a well in a plate and for multiple probe dyes and/or a passive reference (802).

Next, the QC metric determines if data points are consistently missing for multiple probes and over many cycles (804). To be certain, aspects of the present invention look for a consistent drop in the intensity values rather than erratic changes in the intensities. For example, if a well is empty or missing a specific probe then the well should continue to not generate any signal response even after several cycles.

If a sequence of data points is missing, aspects of the present invention indicate that a well in the plate is most likely empty or defective due to consistently low or negligible signal response for each cycle throughout a run or experiment (806). Various aspects of the present invention may also suggest elimination of the data from the wells identified as empty as they might introduce error in the gene expression operations performed subsequently (808). Conversely, if the data measured for a well is not consistently missing or low-valued then aspects of the present invention indicate that the tested wells in a plate are likely not empty or defective and the data results can be used in subsequent gene expression analysis (810).

Figure 9A:
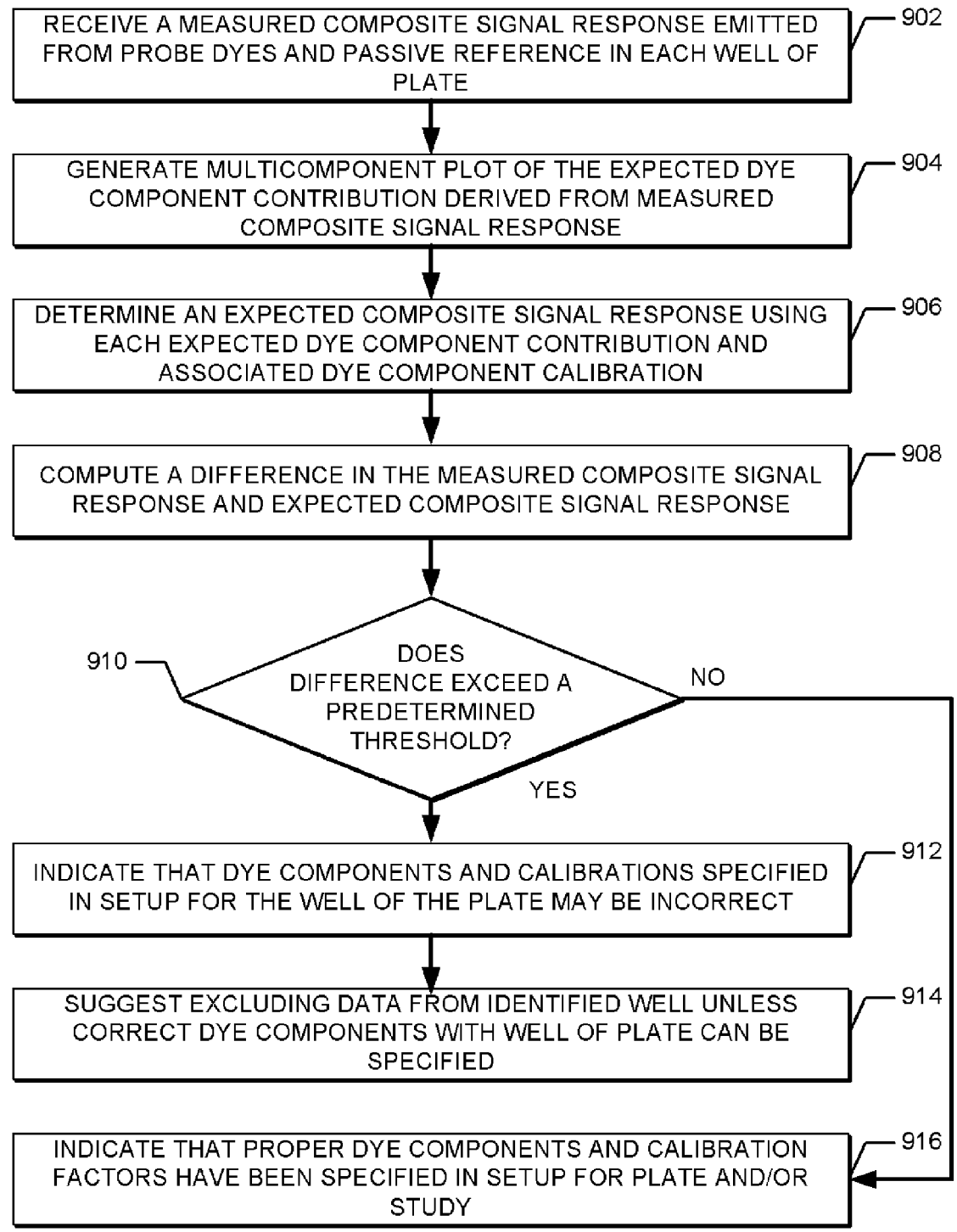
FIG. 9A is another flowchart diagram depicting operations associated with a QC metric for determining a large mean square error (LME) variation according to various implementations of the present invention.

FIG. 9A is another flowchart diagram depicting operations associated with a QC metric for determining a large mean square error (LME) variation. Mean-squared error represents the error that can occur when converting from composite spectral response obtained from the detector to multi-component data. Finding a large mean square (LME) variation can be indicative of the detector instrument being improperly calibrated, specifying incorrect dyes in the configuration and/or a fluorescence measurements outside the capabilities of the detector instrument.

Initially, the QC metric for this condition receives a measured composite signal response emitted from the probe dyes and passive reference in each well of the plate (902). Using Multicomponent analysis, the QC metric generates a multicomponent plot of each expected dye component as derived from the composite signal response (904). Generally, the dye component breakdown depends on the configuration settings in the instrument that identifies the set of dyes being used in the particular assay.

Figure 9B:
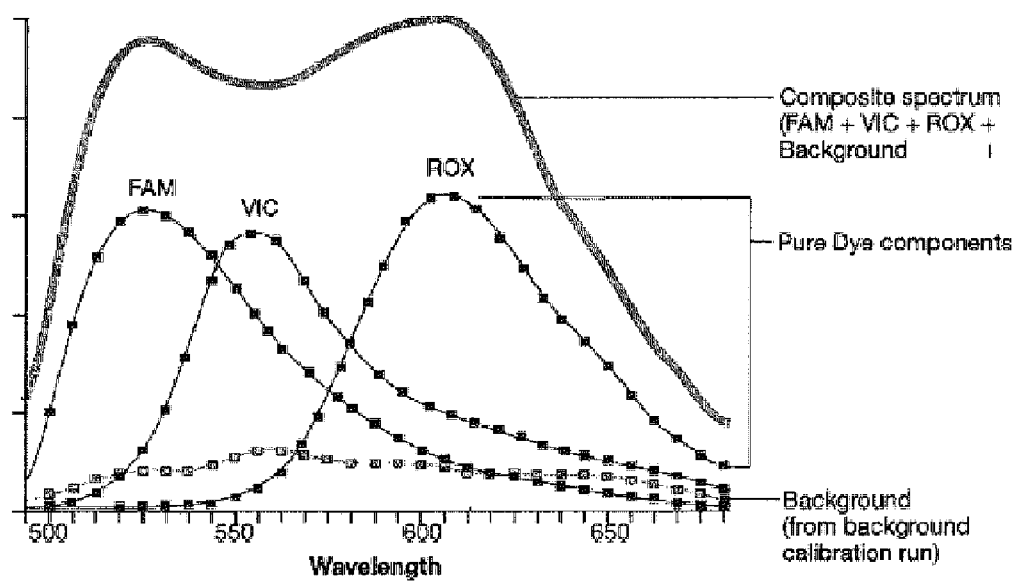
FIG. 9B illustrates a measured composite signal or spectrum received by a detector and the individual dye components determined to have contributed to the composite spectrum using multicomponent analysis in accordance with various implementations of the present invention.

As an illustration of this condition, FIG. 9B depicts the measured composite signal or spectrum and the individual dye components contributing to the composite spectrum derived using multicomponent analysis. There is no mean-squared error (MSE) indicated in FIG. 9B as the composite signal is initially divided into the individual dye components and no comparisons can be made.

The QC metric in FIG. 9A reverses this operation and then determines an expected composite signal response by combining the dye components (906). The expected amplification curve can be derived through a recombination of the individual components in view of the calibration settings and other assumptions for each dye in the assay. To identify a differential, the QC metric in FIG. 9A computes a difference between a measured composite signal response and an expected composite signal response as computed from the individual components (908); the difference between the measured composite signal and expected composite signal response values is identified as the mean-squared error (MSE)

Figure 9C:
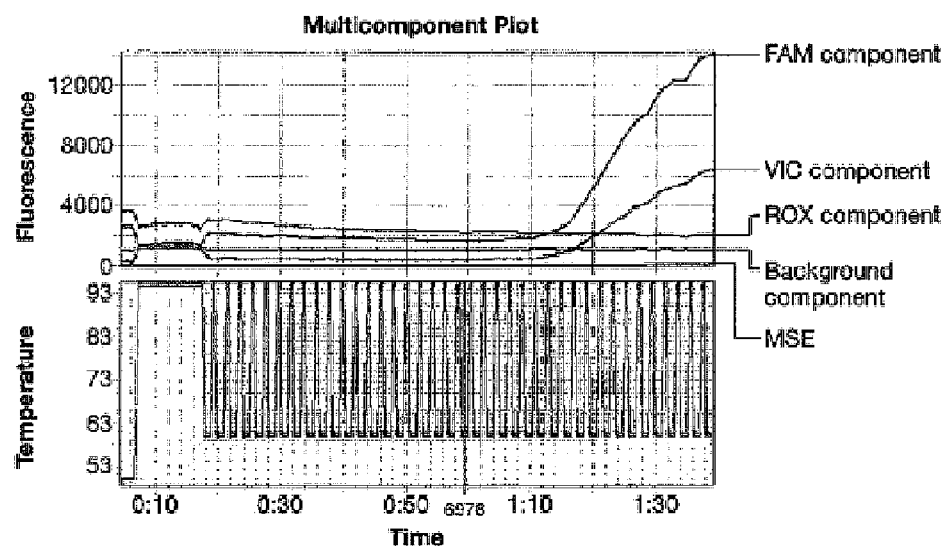
FIG. 9C illustrates an increase in fluorescence for individual dye components as the thermal cycling advances over time according to various implementations of the present invention.

FIG. 9C illustrates the increase in fluorescence for individual dye components as the thermal cycling advances over time. If the detector instrument is calibrated and configured correctly with the proper dye components, a mean-squared error (MSE) should remain relatively constant and small as exemplified in FIG. 9C. When a difference between the expected composite signal response and the measured composite signal response does not exceed a predetermined threshold (910) then the QC metric indicates that the detector has probably been setup and calibrated properly (916). However, when the difference exceeds the acceptable threshold then the QC metric flags the well as potentially holding inaccurate data. The QC metric may indicate that the dye components and calibrations specified in the setup for the well or multiple wells of the plate are incorrect (912). A flag is associated with the well indicating that setup for the well in the plate may be inaccurate (e.g., the wrong set of dyes may have been specified) and need correction. It is also possible that the measured composite signal was off-scale causing a large error in the recreation of the expected composite signal. Consequently, implementations of the invention may suggest excluding data from the identified wells unless the correct dye components could be specified and off-scale measurements shifted within the operating range of the detector (914)

Figure 10:
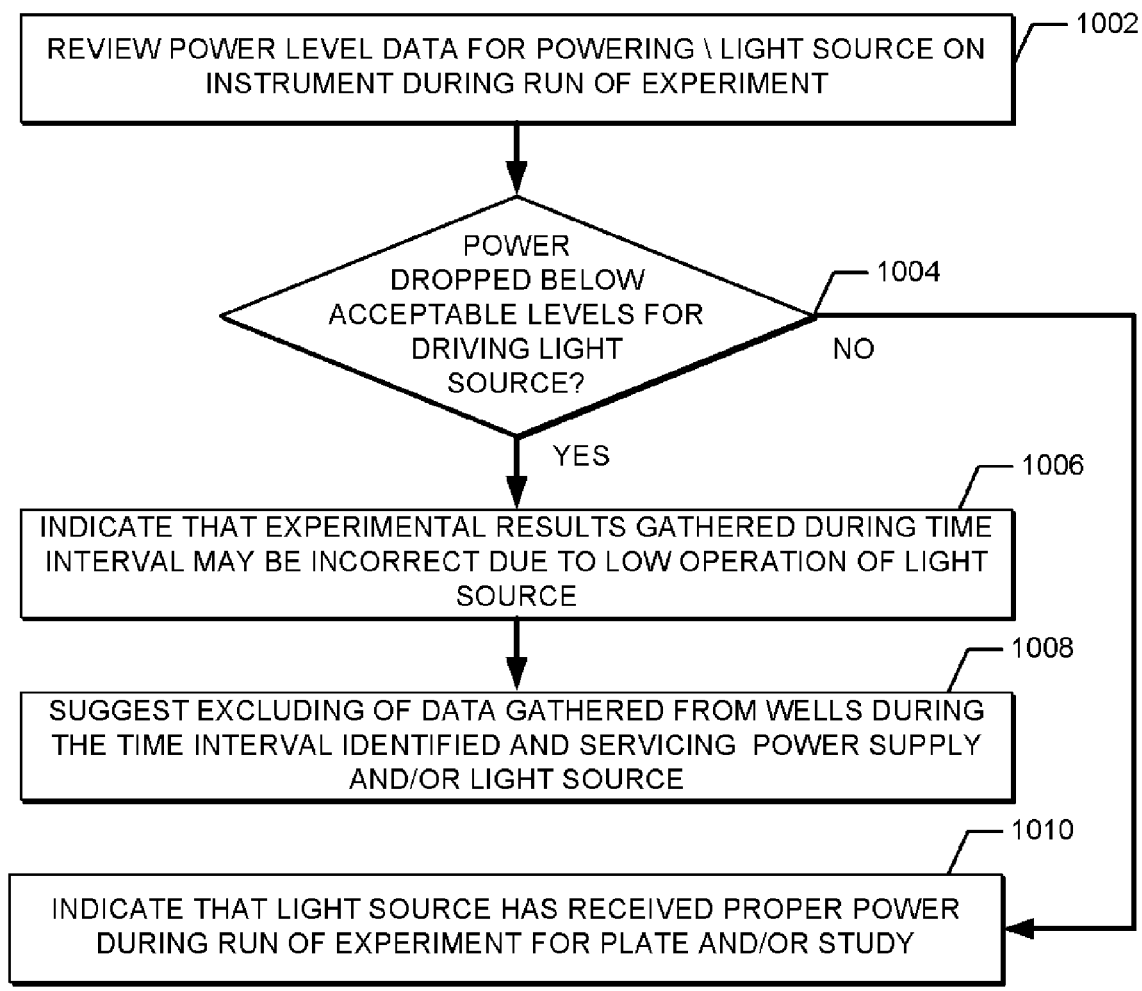
FIG. 10 is flowchart of the operations used by a QC metric measuring the operation of the light source during an experiment in accordance with various implementations of the present invention.

FIG. 10 is another flowchart of the operations used by a QC metric measuring the operation of the light source during an experiment. The QC metric for operation of the light source reviews power level data for powering the light source on the instrument throughout the run of an experiment (1002). It is presumed that a drop in power affects the intensity of the light source and fluorescence measurements associated with the light source. For example, a light source causing probe dyes in RT-PCR to fluoresce may produce inaccurate results if the power source fluctuates and the light source produces varying intensities of light.

Aspects of the present invention identify one or more points in time that the power dropped below acceptable levels for driving the light source (1004). If no drop in power is detected then the QC metric indicates that the light source had received consistent and proper power throughout the experiment and not likely the cause of inaccuracies or errors (1010). Conversely, detected drops in power are correlated with well positions read from the plate as a possible cause of inaccuracies or errors. The QC metric flags and indicates that experimental results gathered from these wells may be incorrect or inaccurate due to lower operating levels of the light source or fluctuation in the intensity of the light source (1006). The same QC metric may also suggest excluding data gathered from one or more of these wells during the time interval identified and potentially servicing the power supply and/or light source of the detector (1008).

Figure 11:
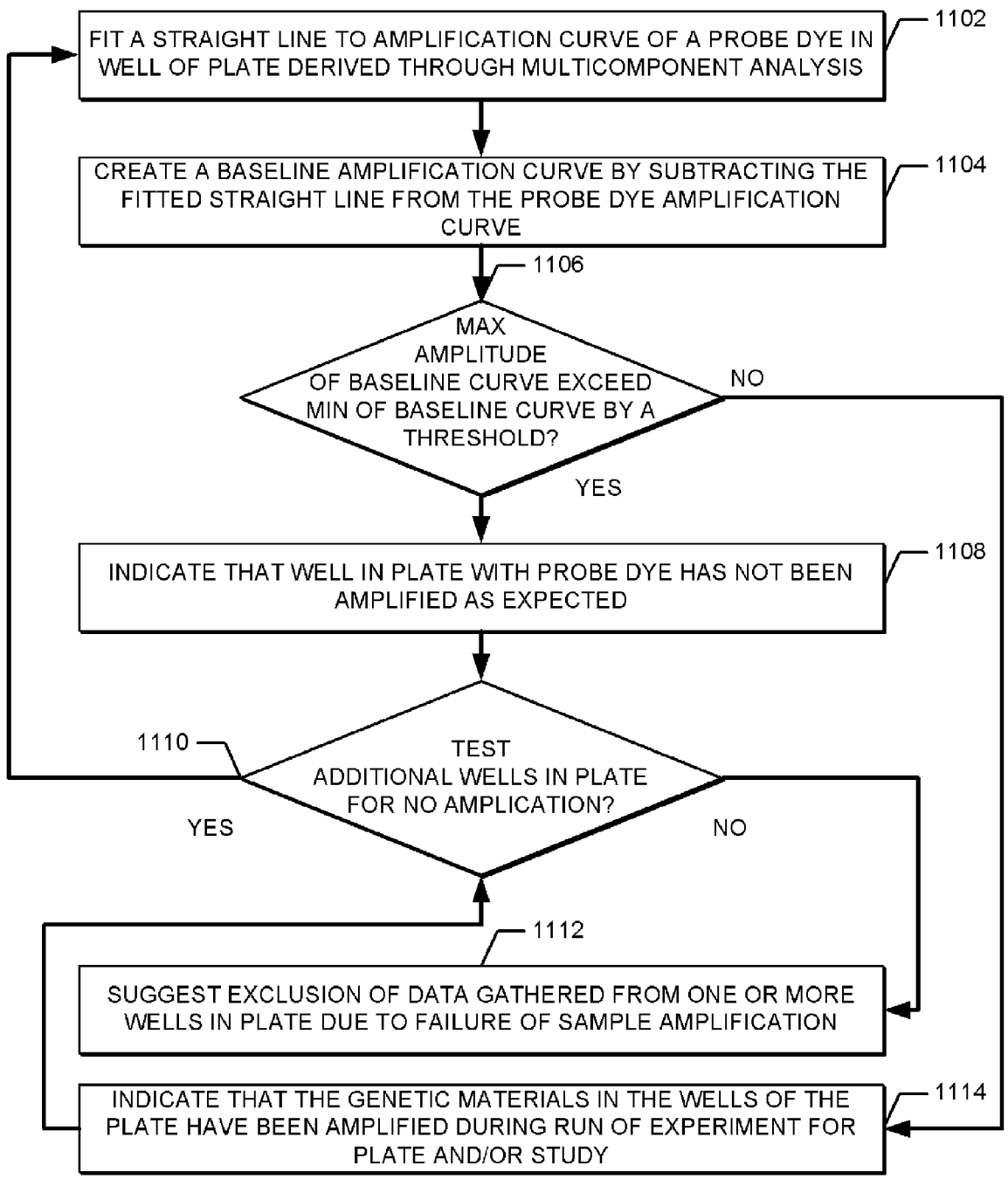
FIG. 11 is a flowchart diagram for a QC metric that identifies when genetic material and probe dyes in a well have not been amplified according to various implementations of the present invention.

FIG. 11 is a flowchart diagram of a QC metric that identifies when genetic material and probe dyes in a well have not been amplified. For example, it is expected that genetic material combined with the probe dyes during RT-PCR will exhibit increased or amplified intensities as the thermocycler operates; failing to exhibit amplified intensities may indicate problems with the test, equipment, samples or no presence of target sequence in sample.

In this case, the QC metric first fits a straight line to an amplification curve of a probe dye derived through multicomponent analysis (1102). A baseline amplification curve is then obtained by subtracting the fitted straight line from the probe dye amplification curve (1104). The baseline amplification curve is used by the subsequent operations herein to identify when wells of samples have not been amplified.

Next, a differential comparison is made between a maximum amplitude of the baseline amplification curve compared with a minimum amplitude of the baseline amplification curve (1106). If the difference between the maximum and minimum amplitude of the baseline amplification curve does not exceed a predetermined minimum threshold, there may be an amplification problem occurring in the particular well. For example, a test for low or no amplification in a well may use a metric condition measured: $\log(\text{Max}_{baseline}/\text{Min}_{baseline}) \leq 1$. In this case, the metric value less than or equal to 1 is a nominal value that may indicate little or no amplification of the sample in the well. If this condition occurs, the QC metric indicates via a flag that the well in the plate with the genetic material and probe dye may not have been amplified or suffers other related problems (1108). Additional wells in the plate may be tested for no amplification (1110 and 1102) or the QC metric may finish the no amplification analysis and indicate that one or more wells should be excluded from gene expression analysis due to no amplification of sample in wells of the plate (1112). This QC metric may also be configured to stop the quality control testing once at least one well is found to have no amplification.

Conversely, the QC metric may use an alternate metric condition measured by: $\log(\text{Max}_{baseline}/\text{Min}_{baseline}) > 1$ to identity when samples in a well have been amplified (1114). In this case, amplification of a target occurs when the resulting metric is greater than 1 as the maximum value in the baseline exceeds the minimum by a non-negligible amount. Once again, various implementations of the present invention may continue to test additional wells in the plate for amplification (1110). Alternatively, the QC metric may finish without testing more wells. The QC metric may indicate that genetic materials in some of the wells in a plate have been amplified and/or study as well as suggesting exclusion of some wells from a plate and/or study due to no detectable amplification of the sample (1112).

Figure 12:
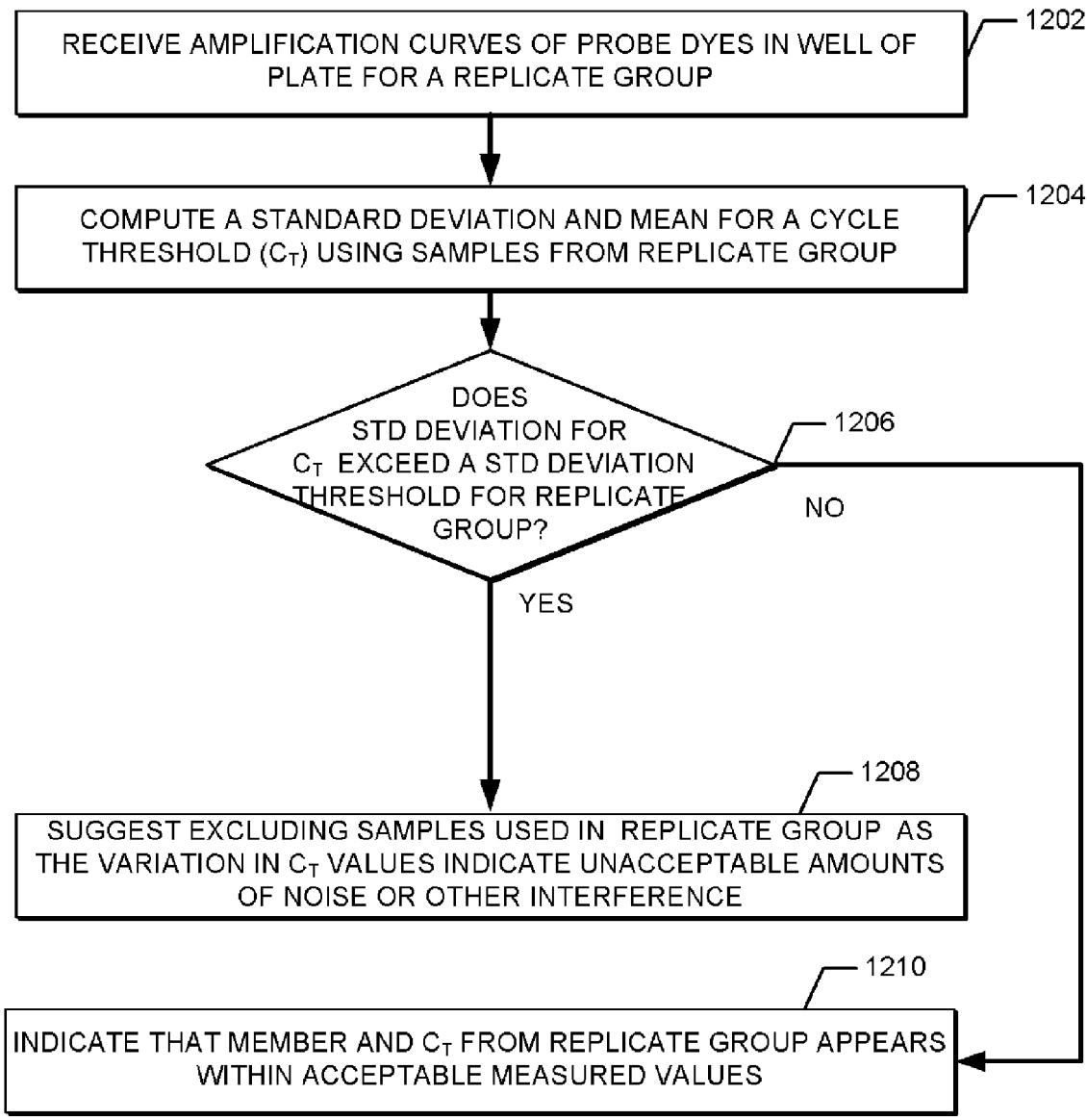
FIG. 12 provides a flowchart diagram for a QC metric that identifies noise based on a high standard deviation of a threshold cycle (Ct) from a replicate group in accordance with various implementations of the present invention.

FIG. 12 provides a flowchart diagram for a QC metric that tests a replicate group of samples for consistent results. Tests on the replicate group include taking multiple readings from the same sample or samples. Inconsistent results from the replicate group helps determine if noise or other factors have rendered the sample data unreliable.

Initially, the QC metric receives an amplification curve of the probe dies in the wells of a plate for a replicate group (1202). The replicate group generally includes multiple readings of samples in a set of wells. Statistical calculations are performed to obtain Ct values for the members of the replicate group. In one implementation, aspects of the present invention computes a mean, a standard deviation and other statistics useful in evaluating the cycle threshold (Ct) and amplification results (1204).

The QC metric for this test depends on the number of standard deviations away from the mean Ct value. When the standard deviation for Ct replicate group exceeds a standard deviation threshold (1206) then the QC metric suggests excluding the samples associated with the replicate group (1208). For example, the samples taken may not be reliable due to excessive noise levels during the sampling and/or other types of interference making the resulting values unreliable. Identifying inconsistent results in the replicate group helps ensure studies do not use data tainted by noise and other types of time-varying interference. Alternatively, the QC metric may indicate that the samples being measured should be kept as the values appear within an acceptable statistical range of values in replicate group (1210). For example, a small standard deviation among the Ct values in the replicate group indicates consistency of the test results and the unlikelihood of excessive noise or other sources of error and/or interference with the sample.

Figure 13:
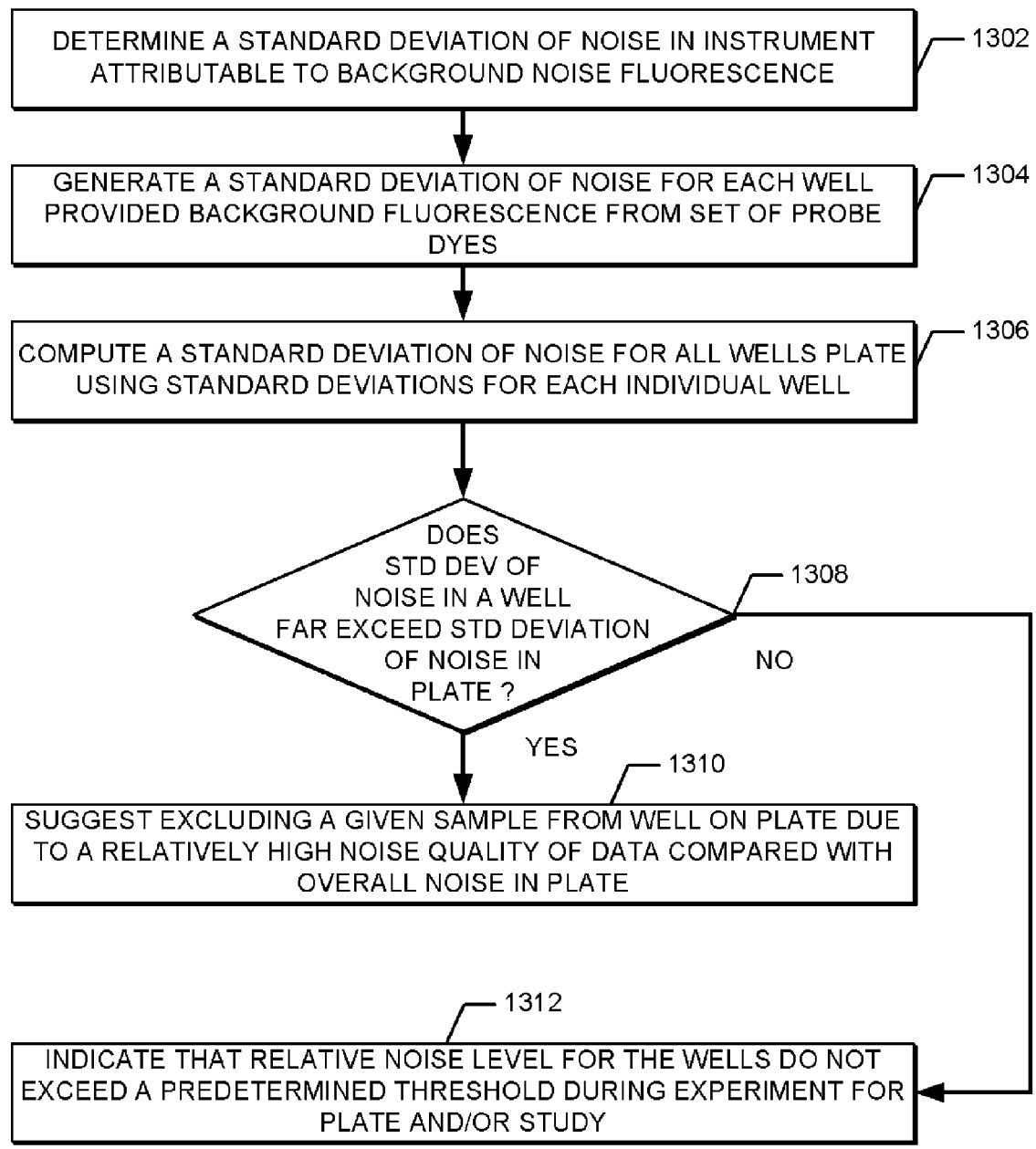
FIG. 13 depicts operations for a QC metric to measure a relative amount of noise in a given well in accordance with various implementations of the present invention.

FIG. 13 depicts operations for a QC metric to measure a relative amount of noise in a given well relative to other wells in a plate. The source of this noise may result from background fluorescence inherent to the instrument and environment surrounding the instrument. Generally, a QC metric determines a standard deviation of noise in instrument attributable to a background noise fluorescence (1302). This may be achieved by measuring the deviation of noise when a well is filled with a buffer or other non-fluorescent material.

Next, the QC metric generates a standard deviation of noise/background fluorescence for the set of probe dyes in each well of the plate (1304). Next, the QC metric computes a standard deviation and a mean value for the set of probe dyes in all wells of plate using the individual standard deviations for each well (1306).

To determine if a sample should be used, the QC metric compares the standard deviation for noise in a well with the standard deviation of noise in the overall plate (1308). When the standard deviation of noise in the well clearly exceeds the overall noise of the plate then the well may have unreliable sample and data. For example, if the standard deviation of background fluorescence in a given well is eight-times greater than the standard deviation of the background fluorescence of the entire plate then there may issues with using data from the samples in the well. QC metric may suggest excluding the given sample from the well on plate due to a relatively high noise quality of data compared with the overall noise in the plate (1310). Alternatively, the QC metric may indicate that the relative noise level for the individual wells do not exceed the threshold level when compared with noise on the plate and therefore could be used in a study (1312).

Figure 14:
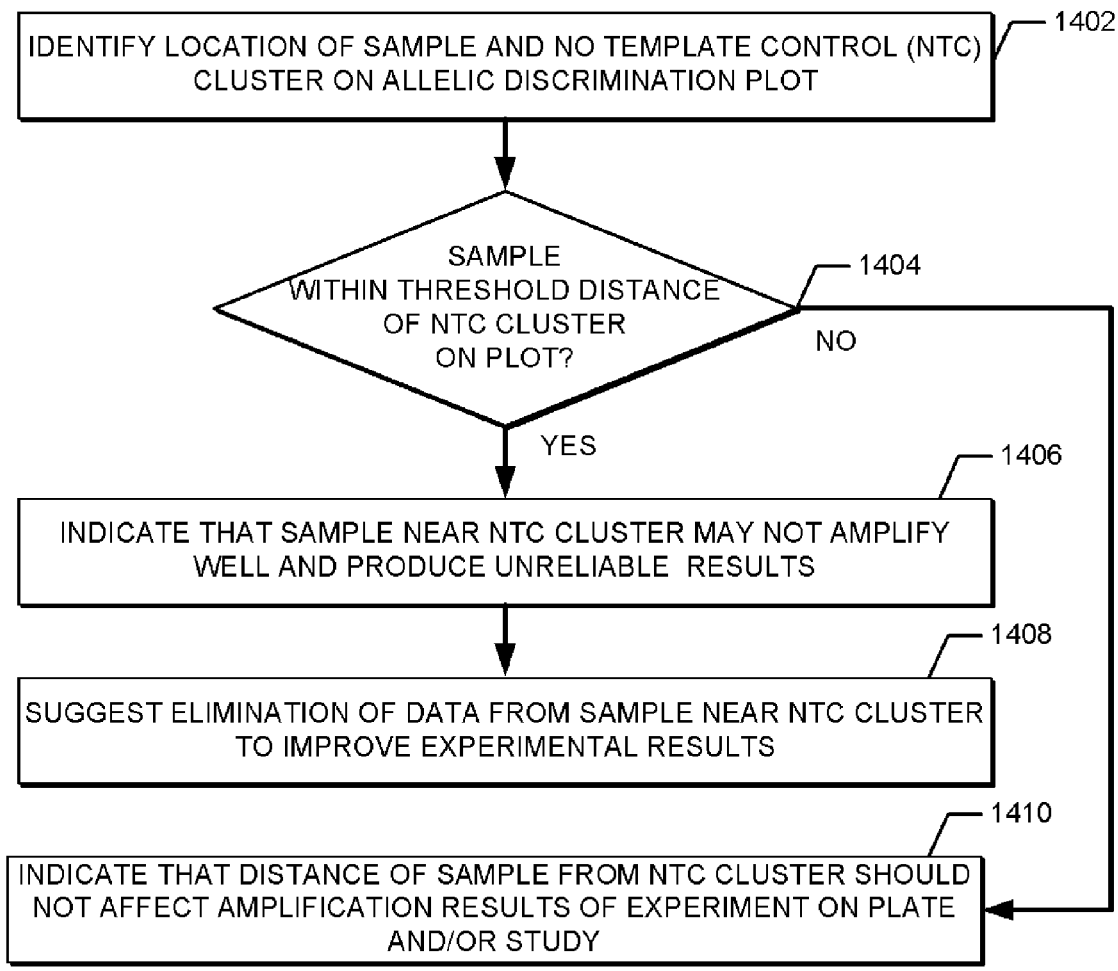
FIG. 14 depicts a QC metric related to cluster analysis for allelic discrimination studies in accordance with various implementations of the present invention.

Another QC metric depicted in the flowchart in FIG. 14 relates to a cluster analysis for allelic discrimination studies.

In general, the allelic discrimination analysis can be improved if unreliable results can be eliminated from the clusters. In this example, the QC metric identifies samples landing near a "no template control" (NTC) cluster. Specifically, this QC metric identifies a distance between a sample allele compared with an NTC cluster on the allelic discrimination plot (1402). This distance is important as samples closer to the NTC cluster generally do not amplify well and tend to introduce unreliable data. Accordingly, if the sample is within a threshold distance of an NTC cluster on the allelic discrimination plot (1404) then the QC metric indicates the sample is not reliable (1406). The QC metric may further suggest excluding the data from the sample near the NTC cluster to improve overall testing results (1408). Alternatively, the QC metric may instead indicate that the distance of the sample from the NTC cluster should not affected amplification results of an experiment for a plate and/or study if it is not beyond this predetermined threshold amount (1410).

Figure 15:
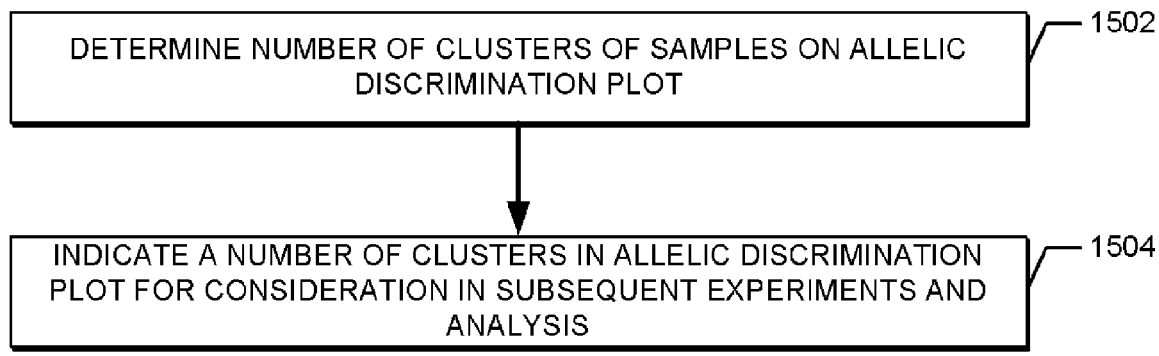
FIG. 15 depicts a flowchart and operations for relating the reliability of an allelic discrimination plot to the number of clusters found in the plot in accordance with various implementations of the present invention.
Figure 16:
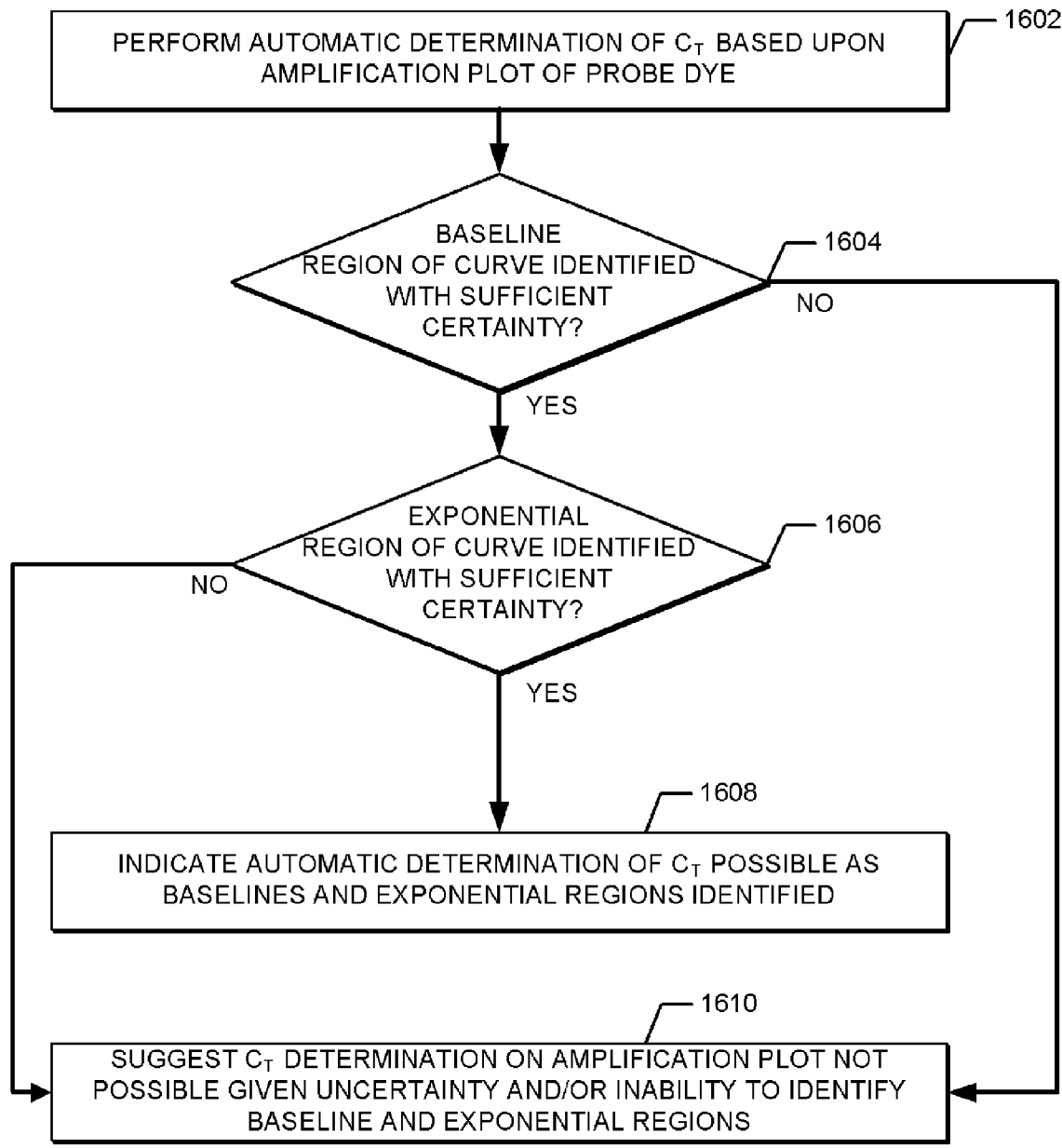
FIG. 16 depicts a flowchart of operations in a QC metric to ensure the validity of a given Ct is valid in accordance with various implementations of the present invention.

Different scientific results may be inferred depending on the number of clusters found in the plot as provided by the operations in FIG. 15. Accordingly, a QC metric may first determine a number of clusters of samples on the allelic discrimination plot (1502). A typical Allelic discrimination plot indicate no clusters or several clusters depending on the details of the actual experiment or study. Accordingly, this QC metric may identify a number of different clusters visually and numerically (1504). The number of clusters may be used for subsequent experiments and analysis. For example, a QC metric indicating 3 clusters may correspond to the presence of g both homozygous and heterozygous alleles FIG. 16 depicts a flowchart of operations in a QC metric to ensure a given Ct is valid. In this example, the QC metric performs automatic determination of Ct based upon an amplification of one or several probe dyes (1602). Typically, multicomponent analysis is used if multiple dyes are combined in each well of plate. The QC metric checks if the baseline region of the curves can be identified and with a sufficient degree of certainty (1604). If the baselines for different dyes cannot be determined (1604) (No-branch) than a suggestion is made that neither can the Ct be determined reliably. Aspects of the present invention may suggest that Ct determination of the amplification plot is not possible given uncertainty and/or inability to identify baseline and exponential regions (1610). However, if baseline regions can be identified (1604) (Yes-branch) then an exponential region on or around the detected Ct value is determined (1606). If the exponential region can also be determined with sufficient certainty (1606) (Yes-branch) then an indication is made that automatic determination of Ct is possible as the baseline and exponential regions were identified (1608). Alternatively, if the exponential region cannot be determined with sufficient certainty (1606) (No-branch) then a suggestion is made that neither can the Ct be determined reliably. Aspects of the present invention may suggest that Ct determination of the amplification plot is not possible given uncertainty and/or inability to identify baseline and exponential regions (1610).

Figure 17:
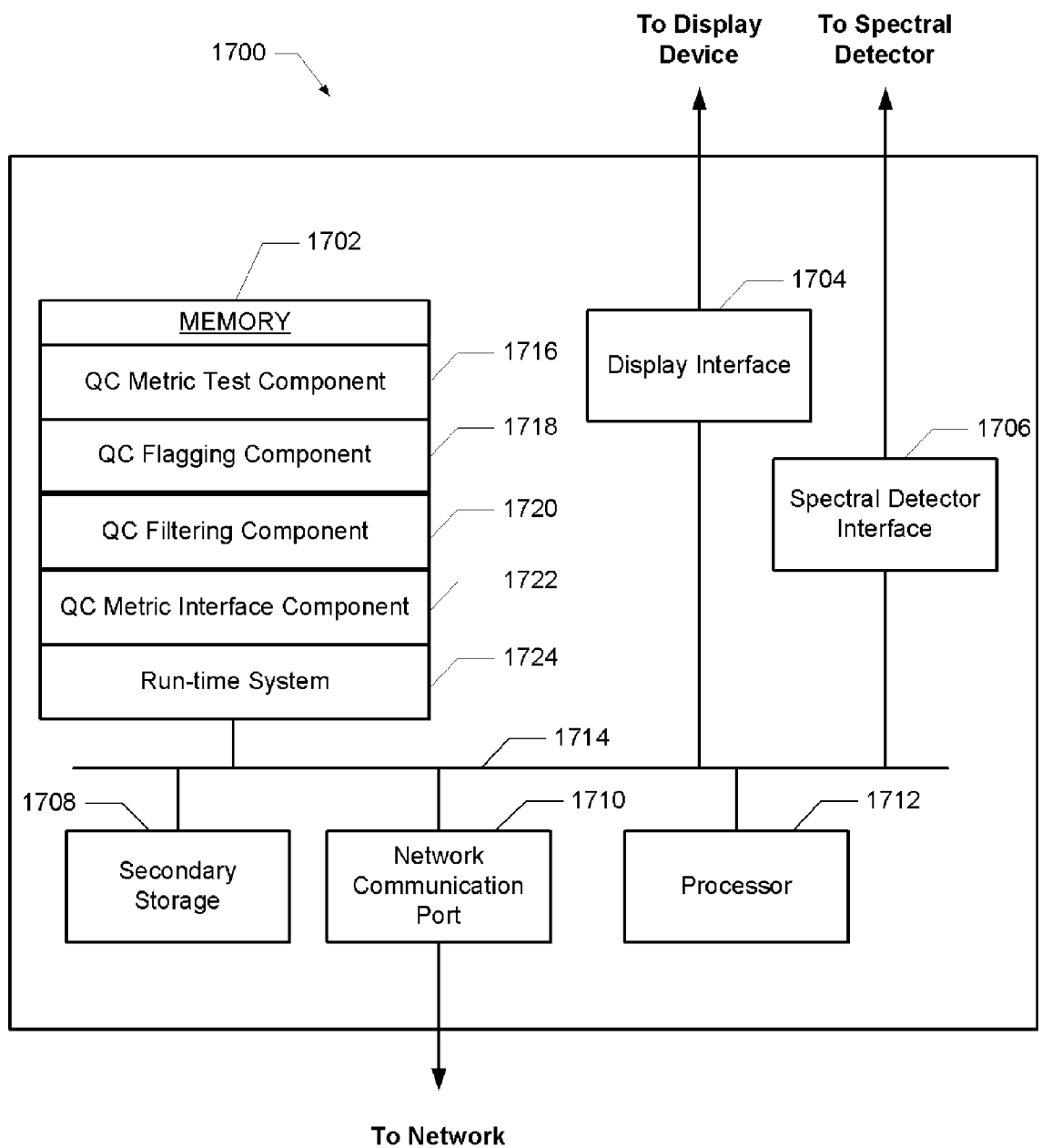
FIG. 17 is a block diagram of a system used in operating an instrument or method in accordance with various implementations of the present invention.

FIG. 17 is a block diagram of a system used in operating an instrument or method in accordance with implementations of the present invention. System 1700 includes a memory 1702 to hold executing programs (typically random access memory (RAM) or read-only memory (ROM) such as Flash), a display interface 1704, a spectral detector interface 1706, a secondary storage 1708, a network communication port 1710, and a processor 1712, operatively coupled together over an interconnect 1714.

Display interface 1704 allows presentation of information related to operation and calibration of the instrument on an external monitor. Spectral detector interface 1706 contains circuitry to control operation of a spectral detector including duplex transmission of data in real-time or in a batch operation. Secondary storage 1708 can contain experimental results and programs for long-term storage including one or more QC storage areas, calibration factors and other data useful in testing, calibrating and performing quality control on data derived from the spectral detector. Network communication port 1710 transmits and receives results and data over a network to other computer systems and databases. Processor 1712 executes the routines and modules contained in memory 1702.

In the illustration, memory 1702 includes a QC metric component 1716, QC metric flagging component 1718, QC metric filtering component 1720, QC metric Interface component 1722 and a run-time system 1724. Run-time system 1724 manages system resources used when processing one or more of the previously mentioned modules. For example, run-time system 1724 can be a general-purpose operating system, an embedded operating system or a real-time operating system or controller.

System 1700 can be preprogrammed, in ROM, for example, using field-programmable gate array (FPGA) technology or it can be programmed (and reprogrammed) by loading a program from another source (for example, from a floppy disk, an ordinary disk drive, a CD-ROM, or another computer). In addition, system 1700 can be implemented using customized application specific integrated circuits (ASICs).

Having thus described various implementations and embodiments of the present invention, it should be noted by those skilled in the art that the disclosures are exemplary only and that various other alternatives, adaptations and modifications may be made within the scope of the present invention. For example, various implementations of the invention are described as being used for gene expression however it is contemplated that the processing, analysis and graphical user interface described can be used directly for or adapted for use in genotyping data, allelic discrimination type studies as well as any other type of biological or genetic analysis.

Embodiments of the invention can be implemented in digital electronic circuitry, or in computer hardware, firmware, software, or in combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs.

Thus, the invention is not limited to the specific embodiments described and illustrated above. Instead, the invention is construed according to the claims that follow and the full scope of their equivalents thereof.

What is claimed is:

1. A computer implemented method of automating quality control for genetic analysis data, comprising:
   receiving genetic analysis data associated with at least one spectral species and genetic sample in each well of a plate;
   performing one or more genetic analysis related operations on the received genetic analysis data derived for each of the wells of the plate;
   identifying at least one of the results from performing the one or more genetic analysis related operations determined to have anomalous characteristics according to a set of one or more quality control metrics; and
   flagging one or more wells of the plate affected by the anomalous characteristics according to the set of one or more quality control metrics and making the resulting flagging of the one or more wells available for further processing.

2. The method of claim 1 further comprising:
   flagging one or more studies using the plate determined to have at least one or more wells flagged for the anomalous characteristics according to quality control metrics, wherein each of the one or more studies uses a set of the one or more wells of the plate.

3. The method of claim 1 wherein the genetic analysis may be selected from a set including: gene expression and genotyping.

4. The method of claim 1 further comprising:
   determining whether to remove selected data associated with the flagged wells based upon the quality control metrics;
   excluding selected flagged data from genetic analysis related operations and indicate flagged wells.

5. The method of claim 3 wherein indicating the flagged wells further includes:
   displaying a first symbol on a visual graphical user interface representation of the plate indicating a well in the plate has not been flagged as anomalous according to one or more quality control metrics; and
   displaying a second symbol on a visual graphical user interface representation of the plate indicating a well in the plate has been flagged as anomalous according to one or more quality control metrics.

6. The method of claim 1 further comprising:
   selecting a set of one or more quality control metrics for automating the quality control of the genetic analysis according to a type of assay and experiment being performed.

7. The method of claim 6 wherein the assay and experiment being performed is selected from a set including: allelic discrimination, absolute quantitation and relative quantitation genotyping.

8. The method of claim 1, wherein the set of one or more quality control metrics is selected from a set of quality control metrics including: a sensor saturation analysis, a bad passive reference analysis, missing data analysis, an empty well analysis, a large composite signal error analysis, a low laser power analysis, a non-amplified well analysis, a non-amplified plate analysis, a noise spike analysis, a high-relative noise analysis, a distance between clusters analysis, Ct failure analysis, a number of clusters analysis, exponential region failure analysis, a Hardy Weinberg analysis, a proportion of outliers analysis, a small sample number in cluster, baselining failure analysis, and thresholding failure analysis.

9. The method of claim 8, wherein the sensor saturation analysis, further comprises:
   determining if a measured intensity level for one or more wells in the plate exceeds a maximum signal response level of a sensor; and
   indicating that the measured intensity from the one or more wells in the plate has exceeded the maximum signal response level of the sensor in response to the determination and may not reflect an accurate measurement.

10. The method of claim 8 wherein the bad passive reference analysis further comprises:
    identifying a start intensity and a subsequent intensity for a passive reference in one or more wells in the plate after a number of thermal cycles;
    determining if a differential between the start intensity and the subsequent intensity for the passive reference in the one or more wells exceeds a predetermined threshold; and
    indicating that the one or more wells in the plate may have failed as the intensity of the passive reference should not vary beyond the predetermined threshold after the number of thermal cycles.

11. The method of claim 8 wherein the missing data analysis further comprises:
    identifying a missing data point for one or more probe dyes and passive reference in one or more wells in the plate during a thermal cycle; and
    indicating that the one or more wells in the plate have missing values for the given thermal cycle may be due to either a failure in system behavior or a mismatch in a configuration.

12. The method of claim 8 wherein the large composite signal error analysis further comprises:
    generating an expected probe dye component contribution derived from a measured composite signal response from probe dyes and a passive reference in each well of the plate;
    determining an expected composite signal response using each of the expected probe dye component contribution in conjunction with associated dye component calibrations; and
    indicating that the probe dye component contribution in the one or more wells in the plate may be incorrectly setup when difference between the measured composite signal response and the expected composite signal response exceeds a predetermined error analysis value.

13. The method of claim 8 wherein the low laser power analysis further comprises:
    reviewing power level data for powering a light source on an instrument during a run of an experiment;
    determining when the power level has dropped below a predetermined acceptable level of driving the light source on the instrument; and
    indicating that the experimental results gathered when driving the light source on the instrument may be incorrect as the power level for operating the light source may have been insufficient.

14. The method of claim 8 wherein the noise-spike analysis further comprises:

receiving an amplification curve of one or more probe dyes derived from a well in the plate;

computing standard deviation and mean noise values for a noise portion of a signal in the amplification curve;

measuring a number of standard deviations that a selected noise point differs from the mean noise value;

determining when the selected noise point on the amplification curve exceeds a predetermined standard deviation threshold compared with the mean noise value for the amplification curve; and indicating that one or more of the selected noise points may reflect a noise spike in the amplification curve and may not reflect a typical noise point on the amplification curve.

15. The method of claim 8 wherein the high relative noise analysis further comprises:

receiving an amplification curve of a first probe dye from each well of a plate derived through multicomponent analysis;

computing a standard deviation and mean value for noise compared with the first probe dye in each well of the plate;

computing a standard deviation and mean for the noise in the plate based upon the mean values and standard deviations of the noise for the first probe dye in each well of the plate;

determining when a standard deviation of noise for the first probe dye in each well of the plate exceeds the mean value of the plate by a threshold number of standard deviations for the plate; and indicating that the one or more wells in the plate may not accurately reflect the amplification characteristics of the probe dye due to a relative amount of noise in the one or more wells compared with the plate.

16. The method of claim 8 wherein the distance between clusters analysis further comprises:

identifying a location of a sample and a no template control (NTC) cluster on an allelic discrimination plot;

determining when the location of the sample is within a threshold distance from the location of the NTC cluster on the allelic discrimination plot; and indicating that one or more values associated with the sample near the NTC cluster may not amplify well and therefore may be unreliable.

17. The method of claim 8 wherein the Ct failure analysis further comprises:

performing an automatic determination of Ct based upon an amplification plot of a probe dye;

determination if at least one or more regions selected from a set including an exponential region and a baseline region of the amplification plot cannot be reliably determined; and indicating the automatic determination of Ct should not be relied upon due to the failure to accurately identify one or more regions of the amplification plot.

18. A computer program product for automating quality control for genetic analysis data, tangibly stored on a computer-readable medium, comprising instructions operable to cause a programmable processor to:

receive genetic analysis data associated with at least one spectral species and genetic sample in each well of a plate;

perform one or more genetic analysis related operations on the received genetic analysis data derived for each of the wells of the plate;

identify at least one of the results from performing the one or more genetic analysis related operations determined to have anomalous characteristics according to a set of one or more quality control metrics; and flag one or more wells of the plate affected by the anomalous characteristics according to the set of one or more quality control metrics and making the resulting flagging of the one or more wells available for further processing.

19. The computer program product of claim 18 further comprising instructions that:

flag one or more studies using the plate determined to have at least one or more wells flagged for the anomalous characteristics according to quality control metrics, wherein each of the one or more studies uses a set of the one or more wells of the plate.

20. The computer program product of claim 18 further comprising instructions that:

determine whether to remove selected data associated with the flagged wells based upon the quality control metrics;

exclude selected flagged data from genetic analysis related operations and indicate flagged wells.

21. The computer program product of claim 18 wherein the genetic analysis may be selected from a set including: gene expression and genotyping.

22. An apparatus for automating quality control for genetic analysis data, comprising:

means for receiving genetic analysis data associated with at least one spectral species and genetic sample in each well of a plate;

means for performing one or more genetic analysis related operations on the received genetic analysis data derived for each of the wells of the plate;

means for identifying at least one of the results from performing the one or more genetic analysis related operations determined to have anomalous characteristics according to a set of one or more quality control metrics; and means for flagging one or more wells of the plate affected by the anomalous characteristics according to the set of one or more quality control metrics and making the resulting flagging of the one or more wells available for further processing.

* * * * *